US011001588B2

(12) United States Patent
Lancia, Jr. et al.

(10) Patent No.: US 11,001,588 B2
(45) Date of Patent: May 11, 2021

(54) ACTIVATING PYRUVATE KINASE R AND MUTANTS THEREOF

(71) Applicant: FORMA Therapeutics, Inc., Watertown, MA (US)

(72) Inventors: David R. Lancia, Jr., Boston, MA (US); Gary Gustafson, Ridgefield, CT (US); Neal Green, Newton, MA (US); Lorna Mitchell, West Beach (AU); Anna Ericsson, Shrewsbury, MA (US); David Richard, Littleton, MA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 16/575,456

(22) Filed: Sep. 19, 2019

(65) Prior Publication Data
US 2020/0087309 A1 Mar. 19, 2020

Related U.S. Application Data

(60) Provisional application No. 62/733,546, filed on Sep. 19, 2018.

(51) Int. Cl.
*C07D 401/14* (2006.01)
*A61K 31/4439* (2006.01)
*C07D 487/04* (2006.01)
*A61K 9/00* (2006.01)

(52) U.S. Cl.
CPC .......... *C07D 487/04* (2013.01); *A61K 9/0053* (2013.01)

(58) Field of Classification Search
CPC ...... A61K 31/4439; A61P 7/00; C07D 401/14
USPC ........................................ 514/338; 546/276.7
See application file for complete search history.

(56) References Cited

U.S. PATENT DOCUMENTS

| | | | |
|---|---|---|---|
| 4,602,093 A | 7/1986 | Baldwin et al. |
| 4,918,073 A | 4/1990 | Ruger et al. |
| 5,030,631 A | 7/1991 | Bauer |
| 5,037,467 A | 8/1991 | Cho et al. |
| 5,059,605 A | 10/1991 | Cough et al. |
| 5,089,621 A | 2/1992 | Kim et al. |
| 5,091,384 A | 2/1992 | Kim et al. |
| 5,180,719 A | 1/1993 | White et al. |
| 5,250,544 A | 10/1993 | Lavielle et al. |
| 5,336,772 A | 8/1994 | Saiki et al. |
| 5,480,899 A | 1/1996 | Yano et al. |
| 5,672,601 A | 9/1997 | Cignarella |
| 5,714,625 A | 2/1998 | Hada et al. |
| 5,747,502 A | 5/1998 | Hanaoka et al. |
| 5,962,703 A | 10/1999 | Moszner et al. |
| 6,214,879 B1 | 4/2001 | Abraham et al. |
| 6,534,501 B2 | 3/2003 | Abraham et al. |
| 6,710,052 B2 | 3/2004 | Pease et al. |
| 6,878,715 B1 | 4/2005 | Klein et al. |
| 7,138,401 B2 | 11/2006 | Kasibhatla et al. |
| 7,160,885 B2 | 1/2007 | Currie et al. |
| 7,875,603 B2 | 1/2011 | Rathinavelu et al. |
| 8,501,953 B2 | 8/2013 | Salituro et al. |
| 8,552,050 B2 | 10/2013 | Cantley et al. |
| 8,692,001 B2 | 4/2014 | Becker et al. |
| 8,742,119 B2 | 6/2014 | Salituro et al. |
| 8,785,450 B2 | 7/2014 | Salituro et al. |
| 8,841,305 B2 | 9/2014 | Thomas et al. |
| 8,877,791 B2 | 11/2014 | Cantley et al. |
| 8,889,667 B2 | 11/2014 | Salituro et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,108,921 B2 | 8/2015 | Cianchetta et al. |
| 9,181,231 B2 | 11/2015 | Su |
| 9,221,792 B2 | 12/2015 | Salituro et al. |
| 9,248,199 B2 | 2/2016 | Metcalf |
| 9,328,077 B2 | 5/2016 | Salituro et al. |
| 9,394,257 B2 | 7/2016 | Ho et al. |
| 9,422,279 B2 | 8/2016 | Metcalf et al. |
| 9,458,132 B2 | 10/2016 | Cianchetta et al. |
| 9,458,139 B2 | 10/2016 | Xu et al. |
| 9,604,999 B2 | 3/2017 | Harris et al. |
| 9,708,267 B2 | 7/2017 | Boxer et al. |
| 9,744,145 B1 | 8/2017 | Liu et al. |
| 9,776,960 B2 | 10/2017 | Xu et al. |
| 9,802,900 B2 | 10/2017 | Li et al. |
| 9,957,250 B2 | 5/2018 | Metcalf et al. |
| 9,981,939 B2 | 5/2018 | Metcalf et al. |
| 10,004,725 B2 | 6/2018 | Dufu et al. |
| 10,017,491 B2 | 7/2018 | Metcalf et al. |

(Continued)

FOREIGN PATENT DOCUMENTS

| | | |
|---|---|---|
| CN | 101812063 A | 8/2010 |
| CN | 102206217 A | 10/2011 |

(Continued)

OTHER PUBLICATIONS

Abbady M.A., et al., Synthesis and biological activity of some new 4-(2-pyrazolin-3-yl)-, 4-(2-isoxazolin-e-yl)- and 4-(1,2,5,6-tetrahydro-2-thioxopyrimidin-4-yl)phenyl aminophenyl sulfides and sulfones., Egyptian Journal of Pharmaceutical Sciences, vol. 27, No. 1-4, (1986), Abstract Only.
Abraham DJ, Mehanna AS, Wireko FC, et al. "Vanillin, a potential agent for the treatment of sickle cell anemia." *Blood*. 1991;77(6):1334-41.
Agrawal RK, Patel RK, Shah V, Nainiwal L, Trivedi B. "Hydroxyurea in sickle cell disease: drug review." *Indian J Hematol Blood Transfus*. Jun. 2014, 30(2):91-96.
Agrawal, R. K. et al., "Hydroxyurea in Sickle Cell Disease: Drug Review", Indian J. Hematol Blood Transfus, 30(2), pp. 91-96, (Apr.-Jun. 2014).

(Continued)

*Primary Examiner* — Charanjit Aulakh
(74) *Attorney, Agent, or Firm* — Barnes & Thornburg LLP

(57) ABSTRACT

The disclosure provides chemical compounds useful as activators of PKR. PKR activating compounds are useful in the treatment of disease and disorders associated with modulation of PKR and/or PKM2, such as pyruvate kinase deficiency (PKD).

15 Claims, 1 Drawing Sheet

(56) References Cited

U.S. PATENT DOCUMENTS

| | | |
|---|---|---|
| 10,034,879 B2 | 7/2018 | Metcalf et al. |
| 10,077,249 B2 | 9/2018 | Li et al. |
| 10,100,040 B2 | 10/2018 | Li et al. |
| 10,100,043 B2 | 10/2018 | Metcalf et al. |
| 10,208,052 B1 | 2/2019 | Zheng et al. |
| 10,266,551 B2 | 4/2019 | Li et al. |
| 10,315,991 B2 | 6/2019 | Xu et al. |
| 10,377,741 B2 | 8/2019 | Metcalf et al. |
| 10,435,393 B2 | 10/2019 | Xu et al. |
| 10,450,269 B1 | 10/2019 | Xu et al. |
| 10,472,371 B2 | 11/2019 | Zheng et al. |
| 10,493,035 B2 | 12/2019 | Dalziel et al. |
| 10,577,345 B2 | 3/2020 | Li et al. |
| 10,675,274 B2 | 6/2020 | Ericsson et al. |
| 10,683,285 B2 | 6/2020 | Li |
| 10,695,330 B2 | 6/2020 | Li et al. |
| 2004/0077648 A1 | 4/2004 | Timmer et al. |
| 2004/0102458 A1 | 5/2004 | Chiosis et al. |
| 2005/0002861 A1 | 1/2005 | Krause et al. |
| 2005/0049263 A1 | 3/2005 | Kasibhatla et al. |
| 2005/0059663 A1 | 3/2005 | Martin et al. |
| 2005/0181305 A1 | 8/2005 | Shibuya |
| 2005/0256103 A1 | 11/2005 | Suzuki et al. |
| 2006/0074121 A1 | 4/2006 | Chen et al. |
| 2006/0211737 A1 | 9/2006 | Huang et al. |
| 2007/0015752 A1 | 1/2007 | Hangauer, Jr. |
| 2007/0270433 A1 | 11/2007 | Brinkman et al. |
| 2008/0058315 A1 | 3/2008 | Cai et al. |
| 2008/0184495 A1 | 8/2008 | Brun et al. |
| 2008/0253965 A1 | 10/2008 | Chiosis et al. |
| 2008/0269234 A1 | 10/2008 | Gandhi et al. |
| 2009/0042966 A1 | 2/2009 | Coleman et al. |
| 2009/0163545 A1 | 6/2009 | Goldfarb |
| 2009/0291921 A1 | 11/2009 | Jabri et al. |
| 2010/0029575 A1 | 2/2010 | Junien et al. |
| 2010/0120863 A1 | 5/2010 | Biftu et al. |
| 2010/0144594 A1 | 6/2010 | Zoller et al. |
| 2010/0144722 A1 | 6/2010 | Alexander et al. |
| 2010/0152157 A1 | 6/2010 | Puech et al. |
| 2010/0179154 A1 | 7/2010 | Almario Garcia et al. |
| 2010/0216774 A1 | 8/2010 | Bender et al. |
| 2010/0324030 A1 | 12/2010 | Dale et al. |
| 2011/0059089 A1 | 3/2011 | Swagemakers et al. |
| 2011/0085969 A1 | 4/2011 | Rollo et al. |
| 2011/0104054 A1 | 5/2011 | Chiosis et al. |
| 2012/0252818 A1 | 10/2012 | Chiosis et al. |
| 2013/0109684 A1 | 5/2013 | Blagg et al. |
| 2013/0116430 A1 | 5/2013 | Fujiwara et al. |
| 2013/0155489 A1 | 6/2013 | Kato et al. |
| 2013/0190315 A1 | 7/2013 | Metcalf et al. |
| 2013/0190316 A1 | 7/2013 | Metcalf et al. |
| 2014/0228360 A1 | 8/2014 | Duncan et al. |
| 2014/0242602 A1 | 8/2014 | Chiosis et al. |
| 2015/0246025 A1 | 9/2015 | Desai et al. |
| 2016/0106728 A1 | 4/2016 | Shen et al. |
| 2016/0200681 A1 | 7/2016 | Yu et al. |
| 2017/0121338 A1 | 5/2017 | Zhang et al. |
| 2017/0216434 A1 | 8/2017 | Hines et al. |
| 2017/0217964 A1 | 8/2017 | Li |
| 2018/0215765 A1 | 8/2018 | Di Giorgio et al. |
| 2019/0218221 A1 | 7/2019 | Zheng et al. |
| 2020/0031839 A1 | 1/2020 | Zheng et al. |
| 2020/0069643 A1 | 3/2020 | Ericsson et al. |
| 2020/0085798 A1 | 3/2020 | Ericsson et al. |
| 2020/0087309 A1 | 3/2020 | Lancia, Jr. et al. |
| 2020/0129485 A1 | 4/2020 | Ericsson et al. |
| 2020/0253939 A1 | 8/2020 | Ericsson et al. |

FOREIGN PATENT DOCUMENTS

| | | |
|---|---|---|
| CN | 102952139 A | 3/2013 |
| CN | 103570722 A | 2/2014 |
| CN | 104736534 A | 6/2015 |
| CN | 105037367 A | 11/2015 |
| CN | 105085528 A | 11/2015 |
| CN | 105153119 A | 12/2015 |
| CN | 105254628 A | 1/2016 |
| CN | 105294694 A | 2/2016 |
| CN | 105348286 A | 2/2016 |
| CN | 106928222 A | 7/2017 |
| CN | 109912610 A | 6/2019 |
| DE | 102008010661 A1 | 9/2009 |
| EP | 0007529 A1 | 2/1980 |
| EP | 0036711 A2 | 9/1981 |
| EP | 0264883 A2 | 4/1988 |
| EP | 0273534 A2 | 7/1988 |
| EP | 0338372 A2 | 10/1988 |
| EP | 0363212 A2 | 4/1990 |
| EP | 0378255 A2 | 7/1990 |
| EP | 0424850 A1 | 5/1991 |
| EP | 0424851 A1 | 5/1991 |
| EP | 0424852 A1 | 5/1991 |
| EP | 0486022 A2 | 5/1992 |
| EP | 0520277 A2 | 12/1992 |
| EP | 0590415 A2 | 4/1994 |
| EP | 0737670 A1 | 10/1996 |
| EP | 1096310 A2 | 5/2001 |
| EP | 1099692 A1 | 5/2001 |
| EP | 1249233 A1 | 10/2002 |
| EP | 1952800 A2 | 8/2008 |
| EP | 3141542 A1 | 3/2017 |
| EP | 2797416 B1 | 8/2017 |
| IN | 1809/MUM/2013 | 5/2013 |
| IN | 2013MU01809 | 3/2015 |
| JP | S 61 200544 | 9/1986 |
| JP | 3 13040 B2 | 2/1991 |
| JP | 3 275666 | 12/1991 |
| JP | 04 054181 A | 2/1992 |
| JP | 05125050 A | 5/1993 |
| JP | 05 196976 | 8/1993 |
| JP | 7 164400 | 6/1995 |
| JP | 1 110376 | 1/1999 |
| JP | 2001261653 A | 9/2001 |
| JP | 2003514673 | 4/2003 |
| JP | 2004175674 A | 6/2004 |
| JP | 2007246885 A | 9/2007 |
| JP | 2007328090 A | 12/2007 |
| JP | 2008031064 A | 2/2008 |
| JP | 2008063256 A | 3/2008 |
| JP | 2009149707 A | 7/2009 |
| JP | 2009212473 A | 9/2009 |
| JP | 2010192782 A | 9/2010 |
| JP | 2011246649 A | 12/2011 |
| JP | 2012188474 A | 10/2012 |
| JP | 2012188475 A | 10/2012 |
| JP | 2013171968 A | 9/2013 |
| KR | 20110096442 A | 8/2011 |
| LB | 11379 | 7/2018 |
| RU | 2517693 C2 | 4/2011 |
| RU | 2472794 C1 | 11/2012 |
| WO | WO 1993/011106 | 6/1993 |
| WO | WO 1993/022298 A1 | 11/1993 |
| WO | WO 1995/019353 A1 | 7/1995 |
| WO | WO 1998/038239 | 9/1998 |
| WO | WO 1998/050364 A1 | 11/1998 |
| WO | WO 1999/001442 A1 | 1/1999 |
| WO | WO 1999/002493 A1 | 1/1999 |
| WO | WO 1999/047489 A1 | 9/1999 |
| WO | WO 1999/047516 A1 | 9/1999 |
| WO | WO 1999/048461 A2 | 9/1999 |
| WO | WO 1999/048490 A1 | 9/1999 |
| WO | WO 1999/065895 A1 | 12/1999 |
| WO | WO 1999/065901 | 12/1999 |
| WO | WO 2000/004023 A1 | 1/2000 |
| WO | WO 2000/021951 A1 | 4/2000 |
| WO | WO 2000/053591 A1 | 9/2000 |
| WO | WO 2001/010842 A2 | 2/2001 |
| WO | WO 2001/032764 | 5/2001 |
| WO | WO 2001/043744 A1 | 6/2001 |
| WO | WO 2001/053288 A2 | 7/2001 |
| WO | WO 2001/057037 A2 | 8/2001 |
| WO | WO 2001/085728 A2 | 11/2001 |
| WO | WO 2002/030358 | 4/2002 |
| WO | WO 2002/034754 A2 | 5/2002 |

(56) References Cited

FOREIGN PATENT DOCUMENTS

| | | |
|---|---|---|
| WO | WO 2002/060902 A1 | 8/2002 |
| WO | WO 2002/076989 A1 | 10/2002 |
| WO | WO 2002/095063 A1 | 11/2002 |
| WO | WO 2003/015769 A1 | 2/2003 |
| WO | WO 2003/037860 A2 | 5/2003 |
| WO | WO 2003/063794 | 8/2003 |
| WO | WO 2003/067332 A2 | 8/2003 |
| WO | WO 2003/084948 A1 | 10/2003 |
| WO | WO 2004/002490 A2 | 1/2004 |
| WO | WO 2004/007770 A2 | 1/2004 |
| WO | WO 2004/009600 A1 | 1/2004 |
| WO | WO 2004/013144 A1 | 2/2004 |
| WO | WO 2004/014374 A1 | 2/2004 |
| WO | WO 2004/014382 | 2/2004 |
| WO | WO 2004/024676 A1 | 3/2004 |
| WO | WO 2004/080457 A1 | 9/2004 |
| WO | WO 2004/089470 A2 | 10/2004 |
| WO | WO 2004/089947 | 10/2004 |
| WO | WO 2004/089947 A2 | 10/2004 |
| WO | WO 2004/104000 A1 | 12/2004 |
| WO | WO 2005/000098 A2 | 1/2005 |
| WO | WO 2005/002577 A1 | 1/2005 |
| WO | WO 2005/009965 A1 | 2/2005 |
| WO | WO 2005/011653 A2 | 2/2005 |
| WO | WO 2005/011656 A2 | 2/2005 |
| WO | WO 2005/016915 A1 | 2/2005 |
| WO | WO 2005/023761 A2 | 3/2005 |
| WO | WO 2005/049570 | 6/2005 |
| WO | WO 2005/058869 | 6/2005 |
| WO | WO 2005/058870 | 6/2005 |
| WO | WO 2005/058871 | 6/2005 |
| WO | WO 2005/058873 | 6/2005 |
| WO | WO 2005/058874 | 6/2005 |
| WO | WO 2005/084667 A1 | 9/2005 |
| WO | WO 2005/094834 A1 | 10/2005 |
| WO | WP 2005/094251 A2 | 10/2005 |
| WO | WO 2005/103015 A1 | 11/2005 |
| WO | WO 2006/002100 A2 | 1/2006 |
| WO | WO 2006/009886 A1 | 1/2006 |
| WO | WO 2006/018279 A2 | 2/2006 |
| WO | WO 2006/018280 A2 | 2/2006 |
| WO | WO 2006/021448 A1 | 3/2006 |
| WO | WO 2006/023608 A2 | 3/2006 |
| WO | WO 2006/034315 A2 | 3/2006 |
| WO | WO 2006/038172 A1 | 4/2006 |
| WO | WO 2006/060122 A2 | 6/2006 |
| WO | WO 2006/084030 A2 | 8/2006 |
| WO | WO 2006/086445 A2 | 8/2006 |
| WO | WO 2006/099884 A1 | 9/2006 |
| WO | WO 2006/101521 A2 | 9/2006 |
| WO | WO 2006/110390 A1 | 10/2006 |
| WO | WO 2006/123121 A1 | 11/2006 |
| WO | WO 2006/130469 A1 | 12/2006 |
| WO | WO 2006/137485 A1 | 12/2006 |
| WO | WO 2007/006926 A2 | 1/2007 |
| WO | WO 2007/007069 A1 | 1/2007 |
| WO | WO 2007/019344 A1 | 2/2007 |
| WO | WO 2007/027734 A2 | 3/2007 |
| WO | WO 2007/042325 | 4/2007 |
| WO | WO 2007/042325 A1 | 4/2007 |
| WO | WO 2007/083119 A2 | 7/2007 |
| WO | WO 2007/087231 A2 | 8/2007 |
| WO | WO 2007/088123 A2 | 8/2007 |
| WO | WO 2007/097931 A2 | 8/2007 |
| WO | WO 2007/098418 A1 | 8/2007 |
| WO | WO 2007/126745 A2 | 11/2007 |
| WO | WO 2007/136603 A2 | 11/2007 |
| WO | WO 2007/138351 A2 | 12/2007 |
| WO | WO 2008/005937 A2 | 1/2008 |
| WO | WO 2008/019139 A2 | 2/2008 |
| WO | WO 2008/032905 A1 | 3/2008 |
| WO | WO 2008/057608 A2 | 5/2008 |
| WO | WO 2008/083027 A1 | 7/2008 |
| WO | WO 2008/094203 A2 | 8/2008 |
| WO | WO 2008/115719 A1 | 9/2008 |
| WO | WO 2008/120003 A1 | 10/2008 |
| WO | WO 2008/135141 A1 | 11/2008 |
| WO | WO 2008/139585 A1 | 11/2008 |
| WO | WO 2009/001126 A1 | 12/2008 |
| WO | WO 2009/004356 A1 | 1/2009 |
| WO | WO 2009/025781 A1 | 2/2009 |
| WO | WO 2009/025784 A1 | 2/2009 |
| WO | WO 2009/063244 A1 | 5/2009 |
| WO | WO 2009/077527 A1 | 6/2009 |
| WO | WO 2009/093032 A1 | 7/2009 |
| WO | WO 2009/112677 | 9/2009 |
| WO | WO 2009/121623 A2 | 10/2009 |
| WO | WO 2009/136889 A1 | 11/2009 |
| WO | WO 2009/153554 A1 | 12/2009 |
| WO | WO 2010/002802 A1 | 1/2010 |
| WO | WO 2010/021717 A2 | 2/2010 |
| WO | WO 2010/028761 A1 | 3/2010 |
| WO | WO 2010/042867 A2 | 4/2010 |
| WO | WO 2010/058318 A1 | 5/2010 |
| WO | WO 2010/092181 A1 | 8/2010 |
| WO | WO 2010/105243 A1 | 9/2010 |
| WO | WO 2010/108268 A1 | 9/2010 |
| WO | WO 2010/115688 A1 | 10/2010 |
| WO | WO 2010/118063 | 10/2010 |
| WO | WO 2010/129596 | 11/2010 |
| WO | WO 2010/132599 A1 | 11/2010 |
| WO | WO 2010/135524 A1 | 11/2010 |
| WO | WO 2010/151797 | 12/2010 |
| WO | WO 2011/002816 | 1/2011 |
| WO | WO 2011/002817 | 1/2011 |
| WO | WO 2011/025690 A1 | 3/2011 |
| WO | WO 2011/037793 A1 | 3/2011 |
| WO | WO 2011/050210 | 4/2011 |
| WO | WO 2011/050211 | 4/2011 |
| WO | WO 2011/060321 A1 | 5/2011 |
| WO | WO 2011/063055 A2 | 5/2011 |
| WO | WO 2011/103256 A1 | 8/2011 |
| WO | WO 2011/116282 A2 | 9/2011 |
| WO | WO 2011/137089 A1 | 11/2011 |
| WO | WO 2011/146358 A1 | 11/2011 |
| WO | WO 2012/002577 A1 | 1/2012 |
| WO | WO 2012/007861 A1 | 1/2012 |
| WO | WO 2012/007868 A2 | 1/2012 |
| WO | WO 2012/007877 A1 | 1/2012 |
| WO | WO 2012/019426 A1 | 2/2012 |
| WO | WO 2012/019427 A1 | 2/2012 |
| WO | WO 2012/056319 A1 | 5/2012 |
| WO | WO 2012/068096 A2 | 5/2012 |
| WO | WO 2012/071519 A1 | 5/2012 |
| WO | WO 2012/071684 A1 | 6/2012 |
| WO | WO 2012/080729 A2 | 6/2012 |
| WO | WO 2012/083246 | 6/2012 |
| WO | WO 2012/088314 | 6/2012 |
| WO | WO 2012/092426 A1 | 7/2012 |
| WO | WO 2012/092442 | 7/2012 |
| WO | WO 2012/092485 A1 | 7/2012 |
| WO | WO 2012/151440 A1 | 11/2012 |
| WO | WO 2012/151448 A1 | 11/2012 |
| WO | WO 2012/151450 A1 | 11/2012 |
| WO | WO 2012/151451 A1 | 11/2012 |
| WO | WO 2012/151452 A1 | 11/2012 |
| WO | WO 2012/160392 | 11/2012 |
| WO | WO 2012/160447 A1 | 11/2012 |
| WO | WO 2012/174126 | 12/2012 |
| WO | WO 2013/003249 A1 | 1/2013 |
| WO | WO 2013/003250 A1 | 1/2013 |
| WO | WO 2013/021054 A1 | 2/2013 |
| WO | WO 2013/038390 A1 | 3/2013 |
| WO | WO 2013/056153 | 4/2013 |
| WO | WO 2013/102142 A1 | 7/2013 |
| WO | WO 2013/102826 A1 | 7/2013 |
| WO | WO 2013/118805 A1 | 8/2013 |
| WO | WO 2013/126856 A1 | 8/2013 |
| WO | WO 2013/127266 A1 | 9/2013 |
| WO | WO 2013/155223 A1 | 10/2013 |
| WO | WO 2013/177224 A1 | 11/2013 |
| WO | WO 2013/184794 A2 | 12/2013 |
| WO | WO 2014/008458 A2 | 1/2014 |
| WO | WO 2014/014050 A1 | 1/2014 |

(56) References Cited

FOREIGN PATENT DOCUMENTS

| WO | WO 2014/018355 A1 | 1/2014 |
|---|---|---|
| WO | WO 2014/023814 A1 | 2/2014 |
| WO | WO 2014/044356 A1 | 3/2014 |
| WO | WO 2014/048865 A1 | 4/2014 |
| WO | WO 2014/061031 A1 | 4/2014 |
| WO | WO 2014/062838 A2 | 4/2014 |
| WO | WO 2014/074848 | 5/2014 |
| WO | WO 2014/102817 A1 | 7/2014 |
| WO | WO 2014/118634 A1 | 8/2014 |
| WO | WO 2014/130890 A1 | 8/2014 |
| WO | WO 2014/139144 A1 | 9/2014 |
| WO | WO 2014/139325 A1 | 9/2014 |
| WO | WO 2014/139978 A1 | 9/2014 |
| WO | WO 2014/144715 A1 | 9/2014 |
| WO | WO 2014/150276 A1 | 9/2014 |
| WO | WO 2014/152588 A1 | 9/2014 |
| WO | WO 2014/172638 A2 | 10/2014 |
| WO | WO 2015/030514 A1 | 3/2015 |
| WO | WO 2015/036078 | 3/2015 |
| WO | WO 2015/042397 A1 | 3/2015 |
| WO | WO 2015/048336 A2 | 4/2015 |
| WO | WO 2015/051230 A1 | 4/2015 |
| WO | WO 2015/054555 A1 | 4/2015 |
| WO | WO 2015/078374 A1 | 6/2015 |
| WO | WO 2015/093948 A2 | 6/2015 |
| WO | WO 2015/116061 A1 | 8/2015 |
| WO | WO 2015/130915 A1 | 9/2015 |
| WO | WO 2015/144605 A1 | 10/2015 |
| WO | WO 2015/172732 A1 | 11/2015 |
| WO | WO 2015/183173 A1 | 12/2015 |
| WO | WO 2015/192701 A1 | 12/2015 |
| WO | WO 2016/005576 A1 | 1/2016 |
| WO | WO 2016/005577 A1 | 1/2016 |
| WO | WO 2016/014324 A1 | 1/2016 |
| WO | WO 2016/014522 A1 | 1/2016 |
| WO | WO 2016/021815 | 2/2016 |
| WO | WO 2016/044604 A1 | 3/2016 |
| WO | WO 2016/044629 A1 | 3/2016 |
| WO | WO 2016/044650 A1 | 3/2016 |
| WO | WO 2016/046837 A1 | 3/2016 |
| WO | WO 2016/047592 A1 | 3/2016 |
| WO | WO 2016/168647 A1 | 10/2016 |
| WO | WO 2016/181408 A2 | 11/2016 |
| WO | WO 2016/196816 | 12/2016 |
| WO | WO 2016/201227 A1 | 12/2016 |
| WO | WO 2017/006270 | 1/2017 |
| WO | WO 2017/050791 A1 | 3/2017 |
| WO | WO 2017/050792 A1 | 3/2017 |
| WO | WO 2017/191274 A2 | 11/2017 |
| WO | WO 2017/214002 A1 | 12/2017 |
| WO | WO 2018/049263 A1 | 3/2018 |
| WO | WO 2018/109277 A1 | 6/2018 |
| WO | WO 2018/175474 A1 | 9/2018 |
| WO | WO 2019/035863 A1 | 2/2019 |
| WO | WO 2019/035864 A1 | 2/2019 |
| WO | WO 2019/035865 A1 | 2/2019 |
| WO | WO 2019/099651 A1 | 5/2019 |
| WO | WO 2019/104134 | 5/2019 |
| WO | WO 2019/113359 | 6/2019 |
| WO | WO 2020/061252 A1 | 3/2020 |
| WO | WO 2020/061255 A1 | 3/2020 |
| WO | WO 2020/061261 A1 | 3/2020 |
| WO | WO 2020/061378 A1 | 3/2020 |
| WO | WO 2020/191022 | 9/2020 |

OTHER PUBLICATIONS

Aiuti, A. et al, Progress and prospects: gene therapy clinical trials (part 2), Gene Ther, 14(22): 1555-1563 (2007).

Al-Hakim, A.K. et al., 14-3-3 cooperates with LKB1 to regulate the activity and localization of QSK and SIK, Journal of Cell Science 118 (23), pp. 5661-5673 (Aug. 2005).

Al-Hakim, A.K. et al., "Control of AMPK-related kinases by USP9X and atypical Lys29/Lys33-linked polyubiquitin chains", Biochemical Journal, 411 (2), pp. 249-260, (Feb. 2008).

Alves-Filho, J.C. & Palsson-Mcdermott, E.M., Pyruvate Kinase M2: A Potential Target for Regulating Inflammation, Frontiers in Immunology, 7(145): Article 145 (2016).

Ambrus, J. et al., Studies on the vasoocclusive crisis of sickle cell disease. III. In vitro and in vivo effect of the pyrimido-pyrimidine derivative, RA-233: studies on its mechanism of action, J Med, 18(3-4):165-198 (1987).

Amer, J. et al., Red blood cells, platelets and polymorphonuclear neutrophils of patients with sickle cell disease exhibit oxidative stress that can be ameliorated by antioxidants, British Journal of Haematology, 132(1):108-113 (2006).

Andresen, C.A. et al., "Protein Interaction Screening for the Ankyrin Repeats and Suppressor of Cytokine Signaling (SOCS) Box (ASB) Family Identify Asb11 as a Novel Endoplasmic Reticulum Resident Ubiquitin Ligase", The Journal of Biological Chemistry, vol. 289, No. 4, pp. 2043-2054, (Jan. 24, 2014).

Ataga KI, Kutlar A, Kanter J, Liles D, Cancado R, Friedrisch J, Guthrie TH, Knight-Madden J, Alvarez OA, Gordeuk VR, Gualandro S, Colella MP, Smith WR, Rollins SA, Stocker JW, Rother RP. "Crizanlizumab for the prevention of pain crises in sickle cell disease." N Engl J Med. Feb. 2, 2017, 376(5):429-439.

Atkinson, Peter J., et al., 3,4-Dihydro-2H-benzoxazinones are 5-HT1A receptor antagonists with potent 5-HT reuptake inhibitory activity, BioOrganic & Medicinal Chemistry Letters, 15(3), pp. 737-741 (2005).

Austin, Nigel E., et al., "Novel 2,3,4,5-tetrahydro-1H-3-benzazepines with high affinity and selectivity for the dopamine D3 receptor", BioOrganic & Medicinal Chemistry Letters, 10(22), pp. 2553-2555, (2000).

Bailey, S.D. et al., "Variation at the NFATC2 Locus Increases the Risk of Thiazolidinedione-Induced Edema in the Diabetes Reduction Assessment with Ramipril and rosiglitazone Medication (DREAM) Study", Diabetes Care, vol. 33, No. 10, pp. 2250-2254, (Oct. 2010).

Bakshi N, Sinha CB, Ross D, Khemani K, Loewenstein G, Krishnamurti L. "Proponent or collaborative: Physician perspectives and approaches to disease modifying therapies in sickle cell disease." PLoS One. Jul. 20, 2017, 12(7):e0178413.

Balakin, Konstantin V. et al., Comprehensive Computational Assessment of ADME Properties using Mapping Techniques, Current Drug Discovery Technologies, 2(2), pp. 99-113 (2005).

Banerjee, S. et al., "Interplay between Polo kinase, LKB1-activated NUAK1 kinase, PP1$\beta$ phosphatase complex and the SCF$\beta^{TrCP}$ E3 ubiquitin ligase", Biochem. J. 461, pp. 233-245, (2014).

Banerjee, T. and Kuypers F.A., Reactive oxygen species and phosphatidylserine externalization in murine sickle red cells, British Journal of Haematology, 124:391-402 (2004).

Barbier AJ, Bodie S, Connor G, et al. "Safety, tolerability, pharmacokinetics and pharmacodynamics of multiple doses of AG-519, an allosteric activator of pyruvate kinase-R, in healthy subjects." Blood. 2016, 128:1264.

Barua, A.K., et al., Chemistry and Industry Communications to the Editor 1376 24 (Oct. 1970).

Bennett, Eric J., et al., "Dynamics of Cullin-Ring Ubiquitin Ligase Network Revealed by Systematic Quantitative Proteomics", Cell 143, pp. 951-965, (Dec. 10, 2010).

Betz T, Lenz M, Joanny JF, Sykes C. "ATP-dependent mechanics of red blood cells." Proc Nod Acad Sci USA. 2009;106(36):15320-5.

Beutler, E. and Gelbart, T., "Estimating the prevalence of pyruvate kinase deficiency from the gene frequency in the general white population", Blood, 95(11): 3585-3588 (2000).

Bianchi, P. and Zanella, A., "Hematologically important mutations: red cell pyruvate kinase", (Third update), Blood Cells Mol Dis., 26(1): 47-53 (2000).

Biftu, T. et al., "Omarigliptin (MK-3102): A Novel Long-Acting DPP-4 Inhibitor for Once-Weekly Treatment of Type 2 Diabetes", Journal of Medicinal Chemistry, 57, pp. 3205-3212, (2014).

Bouwmeester, T. et al., "A physical and functional map of the human TNF-$\alpha$/NF-$\kappa$B signal transduction pathway", Nature Cell Biology, vol. 6, No. 2, pp. 97-105, (Feb. 2004).

(56) References Cited

OTHER PUBLICATIONS

Boxer, M.B. et al., "Evaluation of Substituted N,N[1]-Diarylsulfonamides as Activators of the Tumor Cell Specific M2 Isoform of Pyruvate Kinase", J. Med. Chem., 53: pp. 1048-1055 (2010).

Brajenovic, M. et al., "Comprehensive Proteomic Analysis of Human Par Protein Complexes Reveals an Interconnected Protein Network", The Journal of Biological Chemistry, vol. 275, No. 13, pp. 12804-12811 (Mar. 2004).

Brehme, M. et al., "Charting the molecular network of the drug target Bcr-Abl", PNAS, vol. 106, No. 18, pp. 7414-7419, (May 2009).

Bridges, C.R., et al., "USP9X deubiquitylating enzyme maintains RAPTOR protein levels, mTORC1 signalling and proliferation in neural progenitors", Scientific Reports 7:391, pp. 1-15, (Mar. 2017).

Budzikiewicz, Herbert et al., "Vincetene, a benzopyrroloisoquinoline alkaloid, from *Cynanchum vincetoxicum* (L.) Pers. (*Asclepiadaceae*)", Liebigs Annalen Der Chemie, (8), pp. 1212-1231 (1979).

Buontempo P, Jubin RG, Buontempo C, Real R, Kazo F, O'Brien S, Adeel F, Abuchowski A. "Pegylated carboxyhemoglobin bovine (SANGUINATE) restores RBCs roundness and reduces pain during a sickle cell vaso-occlusive crisis." *Blood*. 2017, 130:969.

Cabrales, P. et al., "A look inside the mechanistic black box: Are red blood cells the critical effectors of RRx-001 cytotoxicity?", Med Oncol., 33(7):63 (2016).

CAS Registry No. 1208929-16-1, Tert-Butyl 1H,2H,3H,4H,5H,6H-Pyrrolo[3,4-C]Pyrrole-2-Carboxylate Hydrochloride (Mar. 11, 2010).

Castilhos, L. et al., "Altered E-NTPDase/E-ADA activities and CD39 expression in platelets of sickle cell anemia patients", Biomed Pharmacother., 79:241-246 (2016).

Castilhos, L. et al., "Increased oxidative stress alters nucleosides metabolite levels in sickle cell anemia", Redox Rep., 22(6):451-459 (2017).

Castilhos, L. et al., "Sickle cell anemia induces changes in peripheral lymphocytes E- NTPDase/E-ADA activities and cytokines secretion in patients under treatment", Biomedicine & Pharmacotherapy 73 (2015), pp. 102-108.

Castro, O., Viability and function of stored sickle erythrocytes, Transfusion, 20(6):695-703 (1980).

Cazzola, M., Pyruvate kinase deficiency, Haematologica, 90(1): 1-2 (2005).

Charache, S. et al., Effect of 2,3-Diphosphateglycerate on oxygen affinity of blood in sickle, Cell Anemia, Journal of Clinical Investigation, 49(4):806-812 (1970).

Chaudhary, Neelam & Maddika, Subbareddy, "WWP2-WWP1 Ubiquitin Ligase Complex Coordinated by PPM1G Maintains the Balance Between Cellular p73 and ΔNp73 Levels", Mol. Cell. Biol. (Oct. 2014).

Cheung, Yiu-Yin et al., Solution-Phase Parallel Synthesis and SAR of Homopiperazinyl Analogs as Positive Allosteric Modulators of MGIu₄, ACS Comb Sci. 13(2), pp. 159-165, (Mar. 2011).

Chiosis et al., Development of a Purine-Scaffold Novel Class of Hsp90 Binders that Inhibit the Proliferation of Cancer Cells and Induce the Degradation of Her2 Tyrosine Kinase, BioOrganic & Medicinal Chemistry, vol. 10, Iss 11, (Nov. 2002), pp. 3555-3564.

Chiou WL, Barve A. "Linear correlation of the fraction of oral dose absorbed of 64 drugs between humans and rats." *Pharm Res*. Nov. 1998, 15(11):1792-5.

Choudhury, N.R., et al., "RNA-binding activity of TRIM25 is mediated by its PRY/SPRY domain and is required for ubiquitination", BMC Biology 15:105, pp. 1-20, (2017).

Chubukov V, Johnson K, Kosinski PA, et al. "Characterization of metabolic response to AG-348, an allosteric activator of red cell pyruvate kinase, in healthy volunteers and pyruvate kinase deficiency patients." Poster presented at: 58th American Society of Hematology Annual Meeting and Exposition; Dec. 4, 2016; San Diego, California. http://investor.agios.com/staticfiles/e1e9fd70-c84b-4472-bff3-bef0ecf05482 Accessed Jul. 28, 2017.

Chung, J.Y.L. et al., "Evolution of a Manufacturing Route to Omarigliptin, A Long-Acting DPP-4 Inhibitor for the Treatment of Type 2 Diabetes", Organic Process Research & Development, 19, pp. 1760-1768, (2015).

Clinical Trials Archive, History of Changes for Study: NCT03815695, A SAD/MAD to Assess the Safety, Pharmacokinetics and Pharmacodynamics of FT-4202 in Healthy Volunteers and Sickle Cell Disease Patients; (Mar. 13, 2019) pp. 1-5.

ClinicalTrlals.gov, NCT03815695, A SAD/MAD to Assess the Safety, Pharmacokinetics and Pharmacodynamics of FT-4202 in Healthy Volunteers and Sickle Cell Disease Patients (Jan. 24, 2019).

ClinicalTrlals.gov, NCT03815695, A SAD/MAD to Assess the Safety, Pharmacokinetics and Pharmacodynamics of FT-4202 in Healthy Volunteers and Sickle Cell Disease Patients (Sep. 17, 2019).

Cloutier, P. et al., "R2TP/Prefoldin-like component RUVBL1/RUVBL2 directly interacts with ZNHIT2 to regulate assembly of U5 small nuclear ribonucleoprotein", Nature Communications, pp. 1-14 (May 2017).

Cole, D.C. et al., Conformationally Constrained N1-arylsulfonyltryptamine derivatives as 5-HT6 receptor antagonists, BioOrganic & Medicinal Chemistry Letters, vol. 15, No. 21, (Nov. 1, 2005), pp. 4780-4785.

Cox, J.L., et al., "The SOX2-Interactome in Brain Cancer Cell Identifies the Requirement of MSI2 and USP9X for the Growth of Brain Tumor Cell", PLOS ONE, vol. 8, Issue 5, pp. 1-13, (May 2013).

Das, A. et al., "USP9X counteracts differential ubiquitination of NPHP5 by MARCH7 and BBS11 to regulate ciliogenesis", PLOS Genetics, pp. 1-24, (May 12, 2017).

Davis, Z.H., et al., "Global Mapping of Herpesvirus-Host Protein Complexes Reveals a Transcription Strategy for Late Genes", Molecular Cell 57, pp. 349-360; (Jan. 22, 2015).

De Furia, F. et al., The effects of cyanate in vitro on red blood cell metabolism and function in sickle cell anemia, J Clin Invest., 51(3):566-574 (1972).

De Jong, K. and Kuypers, F., Sulphydryl modifications alter scramblase activity in murine sickle cell disease, British Journal of Haematology, 133(4):427-432 (2006).

De Rosa MC, Carelli Alinovi C, Galtieri A, Russo A, Giardina B. "Allosteric properties of hemoglobin and the plasma membrane of the erythrocyte: New insights in gas transport and metabolic modulation." IUBMB Life. 2008, 60(2):87-93.

Diez, A. et al., Life-threatening nonspherocytic hemolytic anemia in a patient with a null mutation in the PKLR gene and no compensatory PKM gene expression, Blood, 106:1851 (2005).

Diez-Silva M, Dao M, Han J, Lim CT, Suresh S. "Shape and biomechanical characteristics of human red blood cells in health and disease." MRS Bull. May 2010, 35(5):382-8.

Drissi, R. et al., "Quantitative Proteomics Reveals Dynamic Interactions of the Mini chromosome Maintenance Complex (MCM) in the Cellular Response to Etoposide Induced DNA Damage", Molecular & Cellular Proteomics, pp. 2002-2013, (2015).

Dupont, S. et al., "FAM/USP9x, a Deubiquitinating Enzyme Essential for TGFβ Signaling, Controls Smad4 Monoubiquitination", Cell, 136, pp. 123-135, (Jan. 9, 2009).

Dzandu JK, Johnson RM. "Membrane protein phosphorylation in intact normal and sickle cell erythrocytes." J Biol Chem. Jul. 10, 1980, 255(13):6382-6.

El-Sharief, A.M., et al., Some halogenated sulfonamides with biological interest, Journal of the Indian Chemical Society, vol. 61, No. 6, (1984), pp. 537-543.

Emam, H.A., et al., Heterocyclization of sulfamido chalcones to pyrazoline, cyanopyridone, nicotinonitrile and hydrobenzo [1,2-c] pyrazole derivatives, Journal of the Serbian Chemical Society, vol. 62, No. 7, (1997), Abstract only.

Ernst, A. et al., "A Strategy for Modulation of Enzymes in the Ubiquitin System", Science, 339, pp. 1-15, (Feb. 2013).

Estepp, J.H. et al., A clinically meaningful fetal hemoglobin threshold for children with sickle cell anemia during hydroxyurea therapy, Am J Hematol., 92:1333-1339 (2017).

Fioravanti, R., et al., Synthesis and Biological Evaluation of N-substituted -3, 5-diphenyl—2-pyrazoline derivatives as cyclooxygenase

(56) References Cited

OTHER PUBLICATIONS (COX-2) inhibitors, European Journal of Medicinal Chemistry, vol. 45, No. 12, (Dec. 1, 2010), pp. 6135-6138, XP027526583.
Fitch, R. W. et al., Phantasmidine: An Epibatidine Congener from the Ecuadorian Poison Frog Epipedobates anthonyi', Journal of Natural Products (2010), vol. 73, No. 3, pp. 331-337.
Fleischhacker, W., et al., "Heterocyclic fused naphthalene systems from thebaine. 1", Liebigs Annalen Der Chemie, (5), pp. 844-851, (1983).
Fogeron, M.L. et al., "LGALS3BP regulates centriole biogenesis and centrosome hypertrophy in cancer cells", Nature Communications, 4:1531, pp. 1-14; (2013).
Frost, David A., et al., "Naturally occurring compounds related to phenalenone. V. Synthetic approaches to structures based on 8,9-dihydro-8,8,9-trimethylphenaleno [1,2-b] furan-7-one", Journal of the Chemical Society, Perkin Transactions 1: Organic and Bio-Organic Chemistry (1972-1999), pp. 2159-2169.
Gaudet, P. et al., "Phylogenetic-based propagation of functional annotations within the Gene Ontology consortium", vol. 12, No. 5, pp. 449-462; (Aug. 2011).
Giannone, R.J., et al., "The Protein Network Surrounding the Human Telomere Repeat Binding Factors TRF1, TRF2, and POT1", PLOS One, vol. 5, Issue 8, pp. 1-10, (Aug. 2010).
Gizi, A. et al., Assessment of oxidative stress in patients with sickle cell disease: The glutathione system and the oxidant-antioxidant status, Blood Cells Mol Dis., 46(3):220-225 (2011).
Gladwin, M., Adenosine recepter crossroads in sickle cell disease, Nature Medicine, 17(1):38-40, (2011).
Glombitza, S. et al., Adenosine causes cAMP-dependent activation of chick embryo red cell carbonic anhydrase and 2,3-DPG synthesis, American Journal of Physiology, 271(4):973-81 (1996).
Gomez-Bougie, P. et al., "Noxa controls Mule-dependent Mcl-1 ubiquitination through the regulation of the Mcl-1/USP9X interaction", Biochemical and Biophysical Research Communications 413, pp. 460-464, (2011).
Goncharov, T. et al., "OTUB1 modulates c-IAP1 stability to regulate signaling pathways", The EMBO Journal 32, No. 8, pp. 1103-1114, (2013).
Grace RF, Rose C, Layton DM, Yaish HM, Barcellini W, Galacteros F, Morton DH, Ravindranath Y, Kuo KHM, van Beers EJ, Kwiatkowski JL, Silver BA, Merica E, Kung C, Cohen M, Yang H, Hixon J, Kosinski PA, Silver L, Dang L, Yuan Z, Barbier AJ, Glader B. "Effects of AG_348, a pyruvate kinase activator, on anemia and hemolysis in patients with pyruvate kinase deficiency: Data from the Drive PK study". Blood. 2016, 128:402.
Grasso, D. et al., "Zymophagy, a Novel Selective Autophagy Pathway Mediated by VMP1-USP9x-p62, Prevents Pancreatic Cell Death", The Journal of Biological Chemistry, vol. 286, No. 10, pp. 8308-8324, (Mar. 2011).
Greco, T.M. et al., "Nuclear Import of Histone Deacetylase 5 by Requisite Nuclear Localization Signal Phosphorylation", Molecular & Cellular Proteomics 10: , pp. 1-15, (2011).
Grou, C.P., et al., "Identification of ubiquitin-specific protease 9X (USP9X) as a deubiquitinase acting on the ubiquitin-peroxin 5 (PEX5) thioester conjugate", J. Biol. Chem., pp. 1-24; (Feb. 27, 2012).
Habata, S. et al., "BAG3-mediated Mcl-1 stabilization contributes to drug resistance via interaction with USP9X in ovarian cancer", International Journal of Oncology 49: pp. 402-410, (2016).
Han, K.J. et al., "Ubiquitin-specific Protease 9x Deubiquitinates and Stabilizes the Spinal Muscular Atrophy Protein—Survival Motor Neuron", J. Biol. Chem., pp. 1-22, (Oct. 2012).
Hanson, D. et al., "Identifying biological pathways that underlie primordial short stature using network analysis", Journal of Molecular Endocrinology, pp. 333-344, (2014).
Harada, R. et al., "Structure of pristimerine, a quinonoid triterpene", Tetrahedron Letters, pp. 603-607, (1962).
Harayama, Takashi et al., "Novel synthesis of naphthobenzazepines from N-bromobenzylnaphthylamines by regioselective C-H activation utilizing the intramolecular coordination of an amine to Pd", Synlett, (8), pp. 1141-1144, (2003).
Hauri, S. et al., "Interaction proteome of human Hippo signaling: modular control of the co-activator YAP1", Molecular Systems Biology, 9: 713, pp. 1-16 (Nov. 2013).
Havugimana, P. et al., "A Census of Human Soluble Protein Complexes", Cell 150, pp. 1068-1081, (Aug. 2012).
Hebbel RP, Eaton JW, Balasingam M, Steinberg MH. "Spontaneous oxygen radical generation by sickle erythrocytes." J Clin Invest. 1982, 70(6):1253-9.
Hein, M.Y., et al., "A Human Interactome in Three Quantitative Dimensions Organized by Stoichiometries and Abundances", Cell 163, pp. 712-723, (Oct. 2015).
Hierso, R. et al., Effects of oxidative stress on red blood cell rheology in sickle cell patients, British Journal of Haematology, 166(4):601-606 (2014).
Homan, C.C. et al., "Mutations in USP9X Are Associated with X-linked Intellectual Disability and Disrupt Neuronal Cell Migration and Growth", The American Journal of Human Genetics 94, pp. 470-478, (Mar. 2014).
Hoppe CC, Inati AC, Brown C, et al. "Initial results from a cohort in a phase 2a study (GBT440-007) evaluating adolescents with sickle cell disease treated with multiple doses of GBT440, a HbS polymerization inhibitor." Blood. 2017:130(Suppl 1): 689.
Husain, M.I., et al., Synthesis of some new N-[4-(acetyl/phenyl-5-arylpyrazolin-3-yl)phenyl]arylsulfonamides as oral hypoglycemic agents, Indian Drugs, vol. 24, No. 4, (1987), Abstract only.
Huttlin, E. L., et al., "The BioPlex Network: A Systematic Exploration of the Human Interactome", Cell 162, pp. 425-440, (Jul. 2015).
Huttlin, E.L., et al., "Architecture of the human interactome defines protein communities and disease networks", Nature, pp. 1-35, (May 2017).
Imamura K, Tanaka T. "Multimolecular forms of pyruvate kinase from rat and other mammalian tissues. I Electrophoretic studies." J Biochem. 1972, 71:1043-51.
Imamura K, Tanaka T. "Pyruvate kinase isozymes from rat." Methods Enzymol. 1982, 90:150-65.
International Search Report for PCT/US2019/051831, dated Dec. 6, 2019 (8 pages).
Iwasaki, Tameo et al., "Novel Selective PDE IV Inhibitors as Antiasthmatic Agents. Synthesis and Biological Activities of a Series of 1-Aryl-2,3-bis (hydroxymethyl) naphthalene Lignans", Journal of Medicinal Chemistry (1996), pp. 2696-2704.
Jendralla, H. et al., Synthesis of 1,2,3,4,5,6-Hexahydropyrrolo[3,4-c]pyrrole dihydrobromide and 1,2,3,5-Tetrahydro-2-[(4-Methyl-Phenyl)Sulfonyl]Pyrrolo[3,4-c]Pyrrole, Heterocycles, 41(6): 1291-1298 (1995).
Jin, Y. et al., Effects of gamma irradiation on red cells from donors with sickle cell trait, Transfusion, 37(8):804-808 (1997).
Johansen, L.D., et al., "IKAP localizes to membrane ruffles with filamin a and regulates actin cytoskeleton organization and cell migration", Journal of Cell Science 121, pp. 854-864, (Dec. 2007).
Jones, M.H., et al., "The Drosophila developmental gene fat facets has a human homologue in Xp11.4 which escapes X-inactivation and has related sequences on Yq11.2", Human Molecular Genetics, vol. 5, No. 11, pp. 1695-1701, (Aug. 1996).
Jorgensen, Eugene C., et al., "Thyroxine analogs. 20. Substituted 1-and 2-naphthyl ethers of 3,5-diiodotyrosine", Journal of Medicinal Chemistry 14(11), pp. 1023-1026, (1971).
Joshi, B., et al., Indian J. Chem., Sect. B (1983), 226(2), Abstract only. Chemical Abstract No. 99:105146.
Joshi, P., et al., "The functional interactome landscape of the human histone deacetylase family", Molecular Systems Biology 9, 672, (2013).
Kalai, T. et al., Synthesis of Pyrroline Nitroxide Annulated Carbocycles and Heterocycles, Synthesis No. 6, pp. 831-837 (2000).
Kalfa, et al., FORMA Therapeutics, Inc., Watertown, MA, PowerPointe Presentation, Dated Nov. 6, 2019, *Phase 1 Single and Multiple Ascending Dose Study of the Safety, Tolerability, Pharmacokinetics and Pharmacodynamics of FT-4202, an Allosteric activator of Pyruvate Kinase-R, in Healthy and Sickle Cell Disease Subjects*, 15 pgs.

(56) References Cited

OTHER PUBLICATIONS

Kalfa, T.A. et al., "616 Phase 1 Single (SAD) and Julotiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", (Nov. 2019).
Kaltenbach, L.S., et al., "Huntingtin Interacting Proteins Are Genetic Modifiers of Neurodegeneration", PLOS Genetics, vol. 3, Issue 5, pp. 689-708, (May 2007).
Kasturi, Tirumalai R., et al., "Reactions of tetrahalo-1,2-benzoquinones. III. Reaction of tetrachloro-1,2-benzoquinone withtetralones and naphthols: pathway to the condensates", Journal of the Chemical Society C: Organic, (9), pp. 1257-1259, (1970).
Katzenellenbogen, R.A., et al., "NFX1-123 and Poly(A) Binding Proteins Synergistically Augment Activation of Telomerase in Human Papillomavirus Type 16 E6-Expressing Cells", Journal of Virology, vol. 81, pp. 3786-3796, (Apr. 2007).
Khafagy, M.M., Synthesis of some pyrimidine and pyrazoline derivatives, Al-Azhar Bulletin of Science, vol. 3, No. 1, (1992), Abstract only.
Kharalkar, S.S. et al., Identification of Novel Allosteric Regulators of Human-Erythrocyte Pyruvate Kinase, Chemistry & Biodiversity, vol. 4, pp. 2603-2617 (Feb. 2007).
Kim H, Kosinski P, Kung C, Dang L, Chen Y, Yang H, Chen YS, Kramer J, Liu G. "A fit-for-purpose LC-MS/MS method for the simultaneous quantitation of ATP and 2,3-DPG in human K2EDTA whole blood." J Chromatogr B Analyt Technol Biomed Life Sci. Sep. 1, 2017, 1061-1062:89-96.
Kim J, Lee H, Shin S. "Advances in the measurement of red blood cell deformability: A brief review." J Cell Biotech. 2015;1:63-79.
Kim, M., et al., "Role of Angiomotin-like 2 mono-ubiquitination on YAP inhibition", EMBO reports, vol. 17, No. 1., pp. 64-78, (Nov. 23, 2015).
Kimura, K., et al., "Diversification of transcriptional modulation: Large-scale identification and characterization of putative alternative promoters of human genes", Genome Research 16, pp. 55-65, (2006).
Kirli, K., et al., "A deep proteomics perspective on CRM1-mediated nuclear export and nucleocytoplasmic partitioning", eLife, pp. 1-28; (2015).
Knauff, E.A.H., et al., "Genome-wide association study in premature ovarian failure patients suggests ADAMTS19 as a possible candidate gene", Human Reproduction, vol. 24, No. 9, pp. 2372-2379, (2009).
Kodama, K. et al., Solvent-induced dual chirality switching in the optical resolution of tropic acid via diastereomeric salt formation with (1R,2S)-2-amino-1,2-diphenylethanol, Tetrahedron 70:7923-7928 (2014).
Kristensen, A.R., Gsponer, J. and Foster, L.J., "A high-throughput approach for measuring temporal changes in the interactome", Nat Methods, 9(9), pp. 1-12, (2012).
Kuehl, G. et al., In vitro interactions of 51Cr in human red blood cells and hemolysates, Vox Sang., 40(4):260-272 (1981).
Kung C, Hixon J, Kosinski PA, et al. "AG-348 enhances pyruvate kinase activity in red blood cells from patients with pyruvate kinase deficiency." Blood. 2017;130(11):1347-1356.
Kurita, R. et al., Establishment of Immortalized Human Erythroid Progenitor Cell Lines Able to Produce Enucleated Red Blood Cells, PLOS ONE, vol. 8, Iss.3, pp. 1-15 (Mar. 2013).
Kushwaha, D., et al., "USP9X inhibition promotes radiation-induced apoptosis in non-small cell lung cancer cells expressing mid-to-high MCL1", Cancer Biology & Therapy 16:3, pp. 392-401, (Mar. 2015).
Kwasna, D., et al., "Discovery and Characterization of ZUFSP/ZUP1, a Distinct Deubiquitinase Class Important for Genome Stability", Molecular Cell 70, pp. 150-164, (2018).
Le Quesne, P.W. et al., One-Step Preparation of Tetrakis(bromomethyl)ethylene from Pinacolyl Alcohol, J. Org. Chem., 40(1): 142-143 (1975).
Lehrer-Graiwer J, Howard J, Hemmaway CJ, et al. "Long-term dosing in sickle cell disease subjects with GBT440, a novel HbS polymerization inhibitor." Blood, 2016:128(22): 2488.
Lenihan, J.A., Saha, Orthis, and Young P.W., "Proteomic analysis reveals novel ligands and substrates for LNX1 E3 ubiquitin ligase", PLOS ONE, pp. 1-18; (Nov. 2017).
Li, X., et al., "Defining the protein-protein interaction network of the human protein tyrosine phosphatase family", The American Society for Biochemistry and Molecular Biology, Inc., pp. 1-54, (2016).
Litinov RI, Weisel JW. "Role of red blood cells in haemostasis and thrombosis." ISBT Sci Ser. Feb. 2017, 12(1):176-183.
Liu, X.H., et al., European Journal of Cancer, vol. 31A, No. 6, pp. 953-963, (1995).
Llauger et al., "Evaluation of 8-Arylsulfanyl, 8-Arylsulfoxyl, and 8-Arylsulfonyl Adenine Derivatives as Inhibitors of the Heat Shock Protein 90", J. Med. Chem., 48 (8), pp. 2892-2905, (Mar. 25, 2005).
Llauger et al., "Synthesis of 8-arylsulfoxyl/sulfonyl adenines", Tetrahedron Letters, vol. 45, Issue 52, (Dec. 20, 2004), pp. 9549-9552.
Lochmatter, C. et al., Integrative phosphoproteomics links IL-23R signalling with metabolic adaption in lymphocytes, Scientific Reports, 6:24491 (2016).
Lockwood, S. et al., Endothelium-derived nitric oxide production is increased by ATP released from red blood cells incubated with hydroxyurea, Nitric Oxide, 38:1-7 (2014).
Loriga G. et al., Synthesis of 3,6-diazabicyclo [3.1.1]heptanes as novel ligands for the opioid receptors, Bioorganic & Medicinal Chemistry, Pergamon, GB, vol. 14, No. 3, pp. 676-691, (Feb. 1, 2006).
Lu, L., et al., "The HECT Type Ubiquitin Ligase NEDL2 Is Degraded by Anaphase-promoting Complex/Cyclosome (APC/C)-Cdh1, and Its Tight Regulation Maintains the Metaphase to Anaphase Transition", The Journal of Biological Chemistry, vol. 288, No. 50, pp. 35637-35650; (Dec. 2013).
Lucas, et al., "Facile Synthesis of a Library of 9-Alkyl-8-benzyl-9H-purin-6-ylamine Derivatives", J. Comb. Chem., 3 (6), pp. 518-520, (Sep. 21, 2001).
MacDonald, Gregor J., et al, "Design and Synthesis of trans-3-(2-(4-((3-(3-(5-Methyl-1,2,4-oxadiazolyl))-phenyl(carboxamido)cyclohexyl)ethyl)-7-methylsulfonyl-2,3,4,5-tetrahydro-1H-3-benzazepine (SB-414796): A Potent and Selective Dopamine D3 Receptor Antagonist", Journal of Medicinal Chemistry, 46(23), pp. 4952-4964 (2003).
MacDonald, Rosemary, Red cell 2,3-diphosphoglycerate and oxygen affinity, Anaesthesia, vol. 32, pp. 544-553, (1977).
Martinez-Mayorga Karina et al, Ligand/kappa-opioid receptor interactions: Insights from the X-ray crystal structure, European Journal of Medicinal Chemistry, vol. 66, pp. 114-121 (May 30, 2013).
Mathe-Allainmat, Monique et al., "Synthesis of 2-Amido-2, 3-dihydro-1H-phanalene Derivatives as New Conformationally Restricted Ligands for Melatonin Receptors", Journal of Medicinal Chemistry, 39(16), pp. 3089-3095, (1996).
McCluskey A., et al., BioOrganic & Medicinal Chemistry Letters 10 (2000), pp. 1687-1690.
McCluskey A., et al., Bioorganic & Medicinal Chemistry Letters 11 (2001), pp. 2941-2946.
McGarry, E., et al., "The deubiquitinase USP9X maintains DNA replication fork stability and DNA damage checkpoint responses by regulating CLASPIN during S-phase", Cancerres.aacrjournals.org, pp. 1-39; (2016).
Metcalf B, Chuang C, Dufu K, et al. "Discovery of GBT440, an orally bioavailable R-state stabilizer of sickle cell hemoglobin." ACS Med Chem Lett. 2017; 8(3):321-326.
Meza, N.W. et al, In vitro and in vivo expression of human erythrocyte pyruvate kinase in erythroid cells: a gene therapy approach, Hum Gene Ther, 18(6):502-514 (2007).
Middelkoop, E. et al., Studies on sickled erythrocytes provide evidence that the asymmetric distribution of phosphatidylserine in the red cell membrane is maintained by both ATP-dependent translocation and interaction with membrane skeletal proteins, Biochimica et Biophysica Acta, 937:281-288 (1988).

(56) References Cited

OTHER PUBLICATIONS

Misra H. Bainbridge J, Berryman J, Abuchowski A, Galvez KM, Uribe LF, Hernandez AL, Sosa NR. "A phase 1b open label, randomized, safety study of SANGUINATE™ in patients with sickle cell anemia." Rev Bras Hematol Hemoter. Jan.-Mar. 2017, 39(1):20-7.
Miwa, S. and Fujii, H., Molecular basis of erythroenzymopathies associated with hereditary hemolytic anemia: tabulation of mutant enzymes, Am J Hematol., 51(2): 122-132 (1996).
Moehrle, H., et al., "1,2,3,4-Tetrahydroquinolines as substrates for Mannich compounds", Chemical Sciences, 53(7), pp. 742-752; (1998).
Moriyama R, Lombardo CR, Workman RF, Low PS. "Regulation of linkages between the erythrocyte membrane and its skeleton by 2,3-diphosphoglycerate." J Biol Chem. May 25, 1993, 268(15):10990-6.
Mouchantaf, R., et al., "The Ubiquitin Ligase Itch Is Autoubiquitylated in Vivo and in Vitro but Is Protected from Degradation by Interacting with the Deubiquitylating Enzyme FAM/USP9X", The Journal of Biological Chemistry, vol. 281, No. 50, pp. 38738-38747, (Dec. 2006).
Murn, J. et al., "Control of a neuronal morphology program by an RNA-binding zinc finger protein, Unkempt", Genes & Development 29, pp. 501-512, (2015).
Murray, R.Z., Jolly, L.A., Wood, S.A., "The FAM Deubiquitylating Enzyme Localizes to Multiple Points of Protein Trafficking in Epithelia, where It Associates with E-cadherin and β-catenin", Molecular Biology of the Cell, vol. 15, pp. 1591-1599; (Apr. 2004).
Muzyamba, M. and Gibson, J., Effect of 1-chloro-2,4-dinitrobenzene on K+ transport in normal and sickle human red blood cells, Journal of Physiology, 547(3):903-911 (2003).
Nagai, H., et al., "Ubiquitine-like Sequence in ASK1 Plays Critical Roles in the Recognition and Stabilization by USP9X and Oxidative Stress-Induced Cell Death", Molecular Cell 36, pp. 805-818, (Dec. 2009).
Nagy, Peter I., et al., "Theoretical and Experimental Study on Ion-Pair Formation and Partitioning of Organic Salts in Octanol/Water and Dichloromethane/Water Sytems", Journal of the American Chemical Society, 122 (28), pp. 6583-6593 (2000).
Narayanan, N., Wang, Z., Li, L., and Yang, Y., "Arginine methylation of USP9X promotes its interaction with TDRD3 and its anti-apoptotic activities in breast cancer cells", Cell Discovery 3, pp. 1-17, (2017).
Nathan, J.A., et al., "The Ubiquitin E3 Ligase MARCH7 is Differentially Regulated by the Deubiquitylating Enzymes USP7 and USP9X", Traffic, 9, pp. 1130-1145, (2008).
Neto, E.D. et al., "Shotgun sequencing of the human transcriptome with ORF expressed sequence tags", PNAS, vol. 97, No. 7, pp. 3491-3496, (Mar. 2000).
Noma, T., et al., "Stage- and sex-dependent expressions of Usp9x, an X-linked mouse ortholog of *Drosophila* Fat facets, during gonadal development and oogenesis in mice", Gene Expression Patters 2, pp. 87-91, (2002).
O'Connor, H.F., et al., "Ubiquitin-Activated Interaction Traps (UBAITs) identify E3 ligase binding partners", EMBO reports, vol. 16, No. 12., (2015).
Obach RS. "Prediction of human clearance of twenty-nine drugs from hepatic microsomal intrinsic clearance data: An examination of in vitro half-life approach and nonspecific binding to microsomes." Drug Metab Dispos. Nov. 1999, 27(11):1350-9.
Oksenberg D, Dufu K, Patel MP, Chuang C, Li Z, Xu Q., Silva-Garcia A, Zhou C, Hutchaleelaha A, Patskovska L, Patskovsky Y, Almo SC, Sinha U, Metcalf BW, Archer DR. "GBT440 increases haemoglobin oxygen affinity, reduces sickling and prolongs RBC half-life in a murine model of sickle cell disease." Br J Haematol. Oct. 2016, 175(1):141-53.
Oliviero, G., et al., "The variant Polycomb Repressor Complex 1 component PCGF1 interacts with a pluripotency sub-network that includes DPPA4, a regulator of embryogenesis", pp. 1-11, (2015).
Olsen, J.V., et al., "Global, In Vivo, and Site-Specific Phosphorylation Dynamics in Signaling Networks", Cell 127, pp. 635-648, (Nov. 2006).
Oski, M.D., Frank A., "The Role of Organic Phosphates in Erythrocytes on the Oxygen Dissociation of Hemoglobin," Annals of Clinical Laboratory Science, vol. 1, No. 2 (Nov. 1970), pp. 162-176.
Ould Amar, A.K. et al., Assessment of qualitative functional parameters of stored red blood cells from donors with sickle cell trait (AS) or with heterozygote (AC) status, Transfus Clin Biol., 3(4):225-233 (1996).
Ouyang, W., et al., "β-catenin is regulated by USP9x and mediates resistance to TRAIL-induced apoptosis in breast cancer", Oncology Reports 35, pp. 717-724, (2016).
Paemka, L., et al., "Seizures Are Regulated by Ubiquitin-specific Peptidase 9 X-linked (USP9X), a De-Ubiquitinase", PLOS Genetics, 11(3): pp. 1-16, (Mar. 2015).
Palsson-McDermott, EM et al., Pyruvate kinase M2 regulates Hif-1a activity and IL-1ß induction and is a critical determinant of the Warburg Effect in LPS-activated macrophages, Cell Metabolism, 21:65-80 (2015).
Papp, S.J., et al., "DNA damage shifts circadian clock time via Hausp-dependent Cry1 stabilization", eLIFE, p. 1-19, (2015).
Park, Yoon, Jin, Hyung-seung, and Liu, Yun-Cai, "Regulation of T cell function by the ubiquitin-specific protease USP9X via modulating the Carma 1-Bcl10-Malt1 complex", PNAS, vol. 110, No. 23, pp. 9433-9438, (Jun. 2013).
Pászty C. "Transgenic and gene knock-out mouse models of sickle cell anemia and the thalassemias." Curr Opin Hematol. 1997, 4(2):88-93.
Patel, P., et al., Synthesis of some novel pyrazoline and cyanopyridine derivatives as antimicrobial agents, II Farmaco, vol. 51, No. 1, (1996), Abstract only.
Pavagadhi, T.H., et al., 3-(3'-phenoxyphenylmethyl)-5-aryl-1-acetylpyrazolines, Journal of the Institution of Chemists (India), vol. 73, No. 3, (2001), Abstract only.
Peddaboina, C. et al., "The downregulation of Mcl-1 via USP9X inhibition sensitizes solid tumors to Bcl-xl inhibition", BMC Cancer, 12:541, pp. 1-12, (2012).
Perez-Mancera, P.A., et al., "The deubiquitinase USP9X suppresses pancreatic ductal adenocarcinoma", Nature, 486(7402): pp. 266-270; (Dec. 2012).
Platt OS. "Hydroxyurea for the treatment of sickle cell anemia." N Engl J Med. 2008;358(13):1362-9.
Poillon W., & Kim, B., 2,3-Diphosphoglycerate and intracellular pH as interdependent determinants of the physiologic solubility of deoxyhemoglobin S, Blood, 76:1028-1036 (1990).
Poillon, W. et al., Antisickling effects of 2,3-Diphosphoglycerate Depletion, Blood, 85(11):3289-3296 (1995).
Poillon, W. et al., Intracellular hemoglobin S polymerization and the clinical severity of sickle cell anemia, Blood, 91:1777-1783 (1998).
Poillon, W. et al., The Effect of 2,3-Diphosphoglycerate on the Solubility of Deoxyhemoglobin S1, Archives of Biochemistry and Biophysics, vol. 249, No. 2, pp. 301-305, (Sep. 1986).
PubChem CID: 135338361, create date: Dec. 15, 2018 (Dec. 15, 2018), p. 1, formula.
PubChem CID: 135338378, create date: Dec. 15, 2018 (Dec. 15, 2018), p. 1, formula.
PubChem CID: 69203074, create date: Nov. 30, 2012 (Nov. 30, 2012), pp. 1-20, compound summary.
PubChem CID: 69203505, create date: Nov. 30, 2012 (Nov. 30, 2012), pp. 1-20, compound summary.
Rab, M.A.E. et al., Rapid and reproducible characterization of sickling during automated deoxygenation in sickle cell disease patients, Am. J. Hematol. (2019; 94; pp. 575-584.
Rabai M, Detterich JA, Wenby RB, et al. "Deformability analysis of sickle blood using ektacytometry." Biorheology. 2014;51(2-3):159-70.
Ramdani, G. and Langsley, G., ATP, an Extracellular Signaling Molecule in Red Blood Cells: A Messenger for Malaria?, Biomed Journal, 37(5):284-292 (2014).

(56) References Cited

OTHER PUBLICATIONS

Raththagala, M. et al., Hydroxyurea stimulates the release of ATP from rabbit erythrocytes through an increase in calcium and nitric oxide production, European Journal of Pharmacology, 645(1-3):32-38 (2010).
Rice-Evans C, Omorphos SC, Baysal E. "Cell membranes and oxidative damage." Biochem J. Jul. 1, 1986, 237(1):265-9.
Rosa, M. et al., Allosteric properties of hemoglobin and the plasma membrane of the erythrocyte: New insights in gas transport and metabolic modulation, Life, 60(2):87-93 (2008).
Ross, M.T., et al., "The DNA sequence of the human X chromosome", Nature, 434, pp. 325-337; (Mar. 2005).
Rott, Ruth, et al., "α-Synuclein fate is determined by USP9X-regulated monoubiquitination", PNAS, (2011).
Roy, R., et al., "hnRNPA1 couples nuclear export and translation of specific mRNAs downstream of FGF-2/56K2 signalling", Nucleic Acids Research, vol. 42, No. 20, pp. 12483-12497, (Oct. 2014).
Rush, J., et al., "Immunoaffinity profiling of tyrosine phosphorylation in cancer cells", Nature Biotechnology, vol. 23, No. 1, pp. 94-101, (2005).
Sampson M, Archibong AE, Powell A, et al. "Perturbation of the developmental potential of preimplantation mouse embryos by hydroxyurea." Int J Environ Res Public Health. 2010;7(5):2033-44.
Sato, Y., et al., "Ubiquitin-specific protease 9X in host cells interacts with herpes simplex virus 1 ICP0", J. Vet. Med. Sci. 78(3), pp. 405-410; (2016).
Savio et al., "USP9X Controls EGFR Fate by Deubiquitinating the Endocytic Adaptor Eps15", Current Biology 26, pp. 173-183, (Jan. 2016).
Schwartz, R. et al., Two distinct pathways mediate the formation of intermediate density cells and hyperdense cells from normal density sickle red blood cells, Blood, 92(12):4844- 4855 (1998).
Schwickart, M., et al., "Deubiquitinase USP9X stabilizes MCL1 and promotes tumour cell survival", Nature vol. 463, pp. 103-108; (Jan. 2010).
Sega, M. et al., Fluorescence assay of the interaction between hemoglobin and the cytoplasmic domain of erythrocyte membrane band 3, Blood Cells Mol Dis., 55(3):266-271 (2015).
Shen, G., et al., "MicroRNA-26b inhibits epithelial-mesenchymal transition in hepatocellular carcinoma by targeting USP9X," BMC Cancer 14:393, pp. 1-11, (2014).
Smidrkal, Jan., "Synthesis of fagaronine", Collection of Czechoslovak Chemical Communications, 53(12), pp. 3184-3192, (1988).
Sorathiya, S.D., et al., Preparation and antimicrobial activity of 3-(p-(2',5'-dibromobenzenesulfonamido)phenyl)-5-aryl-1H/acetyl/phenyl-2-pyrazolines, Indian Journal of Chemistry, Section B: Organic, Incl. Medicinal Chemistry, vol. 36B, No. 7, (1997), Abstract only.
Soupene, E. and Kuypers, F., Identification of an erythroid ATP-dependent aminophospholipid transporter, British Journal of Haematology, 133(4):436-438 (2006).
Space SL, Lane PA, Pickett CK, Weil JV. "Nitric oxide attenuates normal and sickle red blood cell adherence to pulmonary endothelium." Am J Hematol. Apr. 2000, 63(4):200-4.
Spinella, J.F., et al., "Genomic characterization of pediatric T-cell acute lymphoblastic leukemia reveals novel recurrent driver mutations", Oncotarget, vol. 7, No. 40, pp. 65485-65503, (Sep. 2016).
Stasiuk, M. et al., Transformations of erythrocytes shape and its regulation, Postepy Biochem., 55(4):425-33 (2009). English Abstract.
St-Denis, N., et al., "Phenotypic and Interaction Profiling of the Human Phosphatases Identifies Diverse Mitotic Regulators", Cell Reports 17, pp. 2488-2501, (Nov. 2016).
Stebbins et al., Crystal Structure of an Hsp90-Geldanamycin Complex: Targeting of a Protein Chaperone by an Antitumor Agent, Cell, (Apr. 1997), 89, p. 241.
Steinberg, Martin H., Pathophysiologically based drug treatment of sickle cell disease, TRENDS in Pharmacological Sciences, vol. 27, No. 4, (Apr. 2006).
Strausberg, R.L., et al., "Generation and initial analysis of more than 15,000 full-length human and mouse cDNA sequences", PNAS vol. 99, No. 26, pp. 16899-16903, (Dec. 2002).
Sun, H., et al., "Bcr-Abl ubiquitination and Usp9x inhibition block kinase signaling and promote CML cell apoptosis", Blood, (Jan. 2011).
Sundd, Prithu et al., Pathophysiology of Sickle Cell Disease, Annual Review of Pathology: Mechanisms of Disease, (Oct. 9, 2018), pp. 261-290.
Swanson, Devin M. et al., "Identification and biological evaluation of 4-(3-trifluoromethylpyridine-2-yl) piperazine-1-c arboxylic acid (5-trifluoromethylpyridin-2-yl) amide, a high affinity TRPV1 (VR1) vanilloid receptor antagonist", Journal of Medicinal Chemistry, 48(6), pp. 1857-1872 (2005).
Taipale, M., et al., "A Quantitative Chaperone Interaction Network Reveals the Architecture of Cellular Protein Homeostasis Pathways", Cell 158, pp. 434-448, (Jul. 2014).
Takenaka, M. et al, Isolation and characterization of the human pyruvate kinase M gene, Eur J Biochem, 198(1):101-106 (1991).
Talmud, P.J., et al., "Gene-centric Association Signals for Lipids and Apolipoproteins Identified via the Human CVD Bead Chip", The American Journal of Human Genetics 85, pp. 628-642, (Nov. 2009).
Tanphaichitr, V.S. et al, Successful bone marrow transplantation in a child with red blood cell pyruvate kinase deficiency, Bone Marrow Transplant, 26(6):689-690 (2000).
Taya, S., et al., "The deubiquitinating enzyme Fam interacts with and stabilizes β-catenin", Genes to Cells 4, pp. 757-767, (1999).
Taya, S., et al., "The Ras Target AF-6 is a Substrate of the Fam Deubiquitinating Enzyme", The Journal of Cell Biology, vol. 142, No. 4, pp. 1053-1062, (Aug. 1998).
Telen, Marilyn, Malik, Punam, and Vercellotti, Gregory M., Therapeutic strategies for sickle cell disease: towards a multi-agent approach, Nature Reviews/Drug Discovery; (Dec. 4, 2018).
Terao, Y., et al., "Trifluoroacetic Acid-Catalyzed 1,3-Cycloaddition of the Simplest Iminium Ylide Leading to 3- or 3,4-Substituted Pyrrolidines and 2,5-Dihydropyrroles", Chem. Pharm. Bull., 33(7), pp. 2762-2766, (1985).
Théard, D., et al., "USP9x-mediated deubiquitination of EFA6 regulates de novo tight junction assembly", The EMBO Journal, vol. 29, No. 9, pp. 1499-1509, (2010).
Thein, Swee Lay, The Molecular Basis of β-Thalassemia, Cold Spring Harb Perspect Med. (2013).
Thompson, Alexis, M.D., M.P.H., "A Targeted Agent for Sickle Cell Disease—Changing the Protein but Not the Gene," The New England Journal of Medicine, (Jun. 14, 2019).
Tian, S., et al., Yaoxue Xueba (1993), 28(11), pp. 870-875. Chemical Abstract No. 120:299229.
Toloczko, A., et al., "Deubiquitinating Enzyme USP9X Suppresses Tumor Growth via LATS kinase and Core Components of the Hippo pathway", Cancer Research, pp. 1-37, (Jul. 2017).
Tripathi, Ashutoshi and Safo, Martin K., In Silico-Screening Approaches for Lead Generation: Identification of Novel Allosteric Modulators of Human-Erythrocyte Pyruvate Kinase, Allostery: Methods and Protocols, Methods in Molecular Biology, Chpt. 19, vol. 796, pp. 351-367 (2012).
Trivigno, D., et al., "Deubiquitinase USP9x Confers Radioresistance through Stabilization of Mcl-1 1,2", NEO Plasia, vol. 14, No. 10, pp. 893-904, (Oct. 2012).
Tsai, Y.C., et al., "Functional Proteomics Establishes the Interaction of SIRT7 with Chromatin Remodeling Complexes and Expands Its Role in Regulation of RNA Polymerase I Transcription", Molecular & Cellular Proteomics 11.5, pp. 60-76, (2012).
Tsutsumi H, Tani K, Fujii H, Miwa S. "Expression of L- and M-type pyruvate kinase in human tissues. Genomics." 1988, 2(1):86-9.
U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Sep. 19, 2019 (v4), 5 pgs.
U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Sep. 23, 2019 (v5), 5 pgs.
U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Oct. 9, 2019 (v6), 5 pgs.

(56) References Cited

OTHER PUBLICATIONS

U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Oct. 10, 2019 (v7), 5 pgs.
U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Nov. 27, 2019 (v8), 5 pgs.
U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Jan. 15, 2020 (v9 ), 5 pgs.
U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Jan. 16, 2020 (v10), 5 pgs.
U.S. National Library of Medicine, *A SAD/MAD to Assess the Safety, Pharmacokinetics and Pharmacodynamics of FT-4202 in Healthy Volunteers and Sickle Cell Disease Patients*, ClinicalTrial Study NCT03815695, Submitted Date: Feb. 21, 2020 (v11), 5 pgs.
Upadhyay J., et al., Studies on pyrazolines. Part III. Preparation and antimicrobial activity of 3-(4-phenylsulfonamidophenyl) -5-aryl-1-ace tyl/phenyl -4,5-dihydropyrazoles, Journal of the Indian Chemical Society, vol. 68, No. 7, (1991), pp. 413-414.
Van Zweiten, R. et al., Inborn defects in the antioxidant systems of human red blood cells, Free Radio Biol Med., 67:377-386 (2014).
Vanderah et al, Novel d-amino acid tetrapeptides produce potent antinociception by selectively acting at peripheral kappa-opioid receptors, European Journal of Pharmacology, Elsevier Science, vol. 583, No. 1, pp. 62-72 (Jan. 24, 2008).
Varjosalo, M., et al., The Protein Interaction Landscape of the Human CMGC Kinase Group, Cell Reports 3, pp. 1306-1320, (Apr. 2013).
Vichinsky, E. et al., "A Phase 3 Randomized Trial of Voxelotor in Sickle Cell Disease," N Engl J Med. DOI: 10.1056/NEJMoa1903212 (Jun. 2019).
Vichinsky, E. et al., Protocol to a Phase 3 Randomized Trial of Voxelotor in Sickle Cell Disease, (Jun. 14, 2019).
Vichinsky, E. et al., Supplementary Appendix to a Phase 3 Randomized Trial of Voxelotor in Sickle Cell Disease, (Jun. 14, 2019).
Vong, Q. P., et al., "Chromosome Alignment and Segregation Regulated by Ubiquitination of Survivin", Science, vol. 310, pp. 1499-1504, (Dec. 2, 2005).
Voskou S, Aslan M, Fanis P, Phylactides M, Kleanthous M. "Oxidative stress in β-thalassaemia and sickle cell disease." Redox Biol. Dec. 2015, 6:226-39.
Wagner, G. et al., Red cell vesiculation—a common membrane physiologic event, J Lab Clin., 108(4):315-324 (1986).
Wan, C., et al., "Panorama of ancient metazoan macromolecular complexes", Nature 525(7569), pp. 339-344, (Sep. 2015).
Wang, G.S., et al., Journal of Ethnopharmacology, 26 (1989), pp. 147-162.
Wang, H. et al., JMJDS regulates PKM2 nuclear translocation and reprograms HIF-1a- mediated glucose metabolism, PNAS, 111(1):279-284 (2014).
Wang, J., et al, "TopBP1 Controls BLM Protein Level to Maintain Genome Stability", Molecular Cell 52, pp. 667-678, (Dec. 2013).
Wang, Q., et al., "The X-linked Deubiquitinase USP9X Is an Integral Component of Centrosome", The American Society for Biochemistry and Molecular Biology, Inc., pp. 1-33, (2017).
Wang, S. et al., "Ablation of the oncogenic transcription factor ERG by deubiquitinase inhibition in prostate cancer", PNAS, vol. 111, No. 11, pp. 4251-4256, (Mar. 2014).
Wang, S., et al., "The ubiquitin ligase TRIM25 targets ERG for degradation in prostate cancer", Oncotarget, vol. 7, No. 40, pp. 64921-64931, (2016).
Wang, X, et al., "Hsp90 Cochaperone Aha1 Downregulation Rescues Misfolding of CFTR in Cystic Fibrosis", Cell 127, pp. 803-815, (Nov. 2006).

Waza et al., Nature, 11, No. 10, (Oct. 2005), pp. 1088-1095.
Weatherall, D., The inherited diseases of hemoglobin are an emerging global health burden, Blood, 115(22): pp. 4331-43336 (2010).
Wei, Wan-Guo et al., "A practical procedure for multisubstituted .beta.-naphthols and their derivatives", Tetrahedron, 59(34), pp. 6621-6625, (2003).
Willcocks, J. et al., Simultaneous determination of low free Mg2+ and pH in human sickle cells using P NMR spectroscopy, The Journal of Biological Chemistry, 277(51):49911-49920 (2002).
Wood BL1, Gibson DF, Tait JF. "Increased erythrocyte phosphatidylserine exposure in sickle cell disease: flow-cytometric measurement and clinical associations." Blood. Sep. 1, 1996, 88(5): pp. 1873-1880.
Woods, N.T., et al., "Charting the Landscape of Tandem BRCT Domain-Mediated Protein Interactions", Sci Signal, 5(242), pp. 1-35, (2014).
Wright, S.W. et al., A Convenient Preparation of Heteroaryl Sulfonamides and Sulfonyl Fluorides from Heteroaryl Thiols, J. Org. Chem., 71: pp. 1080-1084 (2006).
Wu, Y., et al., "Aberrant phosphorylation of SMAD4 Thr277-mediated USP9x-SMAD4 interaction by free fatty acids promotes breast cancer matastasis", Cancer Research, pp. 1-34, (2017).
Wu, Z., et al., "Targeted Ubiquitination and Degradation of G-Protein-Coupled Receptor Kinase 5 by the DDB1-CUL4 Ubiquitin Ligase Complex", PLOS ONE, vol. 7, Issue 8, pp. 1-11, (Aug. 2012).
Xie, Y., et al., "Deubiquitinase FAM/USP9X Interacts with the E3 Ubiquitin Ligase SMURF1 Protein and Protects It from Ligase Activity-dependent Self-degradation", The Journal of Biological Chemistry., vol. 288, No. 5, pp. 2976-2985, (Feb. 2013).
Xu, Z., et al., "Identification of a Deubiquitinating Enzyme as a Novel AGS3-Interacting Protein", PLOS One, vol. 5, Issue 3, pp. 1-12, (Mar. 2010).
Yan, J., et al., "Usp9x- and Noxa-mediated Mcl-1 downregulation contributes to pemetrexed-induced apoptosis in human non-small-cell lung cancer cells", Cell Death and Disease 5, pp. 1-7, (2014).
Yang H, Merica E, Chen Y, Cohen M, Goldwater R, Hill C, et al. "Phase I single (SAD) and multiple ascending dose (MAD) studies of the safety, tolerability, pharmacokinetics (PK) and pharmacodynamics (PD) of AG-348, a first-in-class allosteric activator of pyruvate kinase-R, in healthy subjects." Blood. (2014), 124: 4007.
Yang H, Merica E, Chen Y, et al. "Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers." Clin Pharmacol Drug Dev. Aug. 9, 2018.
Yi, S., et al., Leukemia Research, vol. 15(10), (1991), pp. 883-886.
You, J. and Pickart, C.M., "A HECT Domain E3 Enzyme Assembles Novel Polyubiquitin Chains", vol. 276, No. 23, pp. 19871-19878, (2001).
Yu, W., et al., "Large-Scale Concatenation cDNA Sequencing", Genome Research 7, pp. 353-358, (1997).
Zanella A, Fermo E, Bianchi P, Chiarelli LR, Valentini G. "Pyruvate kinase deficiency: The genotype-phenotype association." Blood Rev. (2007), 23: pp. 217-231.
Zanella A, Fermo E, Bianchi P, Valentini G. "Red cell pyruvate kinase deficiency: molecular and clinical aspects." Br J Haematol. 2005; 130(1): pp. 11-25.
Zhang, C., et al., "Synergistic anti-tumor activity of gemcitabine and ABT-737 in vitro and in vivo through disrupting the interaction of USP9X and Mcl-1", Molecular Cancer Therapeutics, (May 12, 2011).
Zhang, C., et al., "USP9X destabilizes pVHL and promotes cell proliferation", Oncotarget, vol. 7, No. 37, pp. 60519-60534, (2016).
Zhang, Y & Xia, Y., Adenosine signaling in normal and sickle erythrocytes and beyond, Microbes Infect., 14(10) (2012).
Zhang, Y. et al., Detrimental effects of adenosine signaling in sickle cell disease, Nature Medicine, 17(1): pp. 79-87 (2011).
Zhang, Yongmin et al., "Organic reactions in chiral micelles. 7. The structural effects on the asymmetric oxidation of prochiral sulfides in chiral micelles", Chinese Journal of Chemistry, (1990), pp. 89-96.
Zhao, Y., et al., "Noncanonical regulation of alkylation damage resistance by the OTUD4 deubiquitinase", EMBO Journal, vol. 34, No. 12, pp. 1687-1703, (2015).

(56) References Cited

OTHER PUBLICATIONS

Zhi et al., Hybrid Antibacterals. DNA Polymerase—Topoisomerase Inhibitors. J. Med. Chem., published on Web Jan. 25, 2006., vol. 49, pp. 1455-1465, especially p. 1456. Scheme 3, compound 4; p. 1457, Scheme 4, compound 13, p. 1462.
Zhou, L., et al., "The Scaffold Protein KSR1, A Novel Therapeutic Target for the Treatment of Merlin-Deficient Tumors", Oncogene 35(26), pp. 3443-3453, (Jun. 2016).
Zhou, ZH et al., Phosphorus, Sulfur and Silicon and the Related Elements (1999), 152, pp. 45-52. Chemical Abstract No. 132: 180853.
Zhu, Tong et al., Polymer-Supported Synthesis of Pyridone-Focused Libraries as Inhibitors of Anaplastic Lymphoma Kinase, Journal of Combinatorial Chemistry, 8(3) (2006), pp. 401-409.
Verma, S.K. et al., Imidazole-Catalyzed Monoacylation of Symmetrical Diamines, Organic Letters, 12(19):4232-4235 (201), Apr. 17, 2010.
Keun-Soo Nam et al., "Synthesis of quinolone antimicrobial agents and their antibacterial activities," 5 Korean J. Med. Chem. 2-5 (1995).
Adakveo [package insert]. East Hanover, New Jersey, Novartis Pharmaceuticals Corporation (Nov. 2019), 10 pgs.
Agios First Quarter 2020 Financial Results (Apr. 30, 2020), pp. 1-22.
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *Blood* (2020) 136 (Supplement 1):19-20, Nov. 4, 2020.
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *ASH* 2020, Dec. 7, 2020.
Chen, Yue et al.—Preclinical Pharmacokinetic/Pharmacodynamic Relationships for AG-348, An Investigational Small-Molecule Activator of Pyruvate Kinase, European Hematology Association, Jun. 13, 2015.
Chonat, S. et al.,—Improvement in Red Blood Cell Physiology in Children With Sickle Cell Anemia Receiving Voxelotor—Childrens Healthcare of Atlanta (Dec. 2019).
Christensen, R.D. et al., Siblings with Severe Pyruvate Kinase Deficiency and a Complex Genotype, American Journal of Medical Genetics, Part A, (2016), pp. 2449-2452.
Clinical Trial Study—NCT02604433—U.S. National Library of Medicine, An Efficacy and Safety Study of Luspatercept (ACE-536) Versus Placebo in Adults Who Require Regular Red Blood Cell Transfusions Due to Beta ($\beta$) Thalassemia (BELIEVE), Submitted Date: Nov. 13, 2015, 24 pgs.
Clinical Trial Study—NCT03815695—U.S. National Library of Medicine, A SAD/MAD to Assess the Safety, Pharmacokinetics and Pharmacodynamics of FT-4202 in Healthy Volunteers and Sickle Cell Disease Patients, Submitted Date: Sep. 19, 2019 (v4), 5 pgs.
Clinical Trial Study NCT03815695—U.S. National Library of Medicine, A SAD/MAD to Assess the Safety, Pharmacokinetics and Pharmacodynamics of FT-4202 in Healthy Volunteers and Sickle Cell Disease Patients, Submitted Apr. 1, 2020, (v12), 12 pgs.
ClinicalTrials.gov, NCT03815695 (v13), "A SAD/MAD to Assess the Safety, Pharmacokinetics and Pharmacodynamics of FT-4202 in Healthy Volunteers and Sickle Cell Patients," Jun. 17, 2020.
ClinicalTrials.gov, NCT03815695 (v14), "A SAD/MAD to Assess the Safety, Pharmacokinetics and Pharmacodynamics of FT-4202 in Healthy Volunteers and Sickle Cell Patients," Jul. 17, 2020.
ClinicalTrials.gov, NCT03815695 (v15), "A SAD/MAD to Assess the Safety, Pharmacokinetics and Pharmacodynamics of FT-4202 in Healthy Volunteers and Sickle Cell Patients," Aug. 20, 2020.
ClinicalTrials.gov, NCT03815695 (v16), "A SAD/MAD to Assess the Safety, Pharmacokinetics and Pharmacodynamics of FT-4202 in Healthy Volunteers and Sickle Cell Patients," Sep. 3, 2020.
ClinicalTrials.gov, NCT03815695 (v17), "A SAD/MAD to Assess the Safety, Pharmacokinetics and Pharmacodynamics of FT-4202 in Healthy Volunteers and Sickle Cell Patients," Sep. 22, 2020.
ClinicalTrials.gov, NCT03815695 (v18), "A SAD/MAD to Assess the Safety, Pharmacokinetics and Pharmacodynamics of FT-4202 in Healthy Volunteers and Sickle Cell Patients," Oct. 19, 2020.
ClinicalTrials.gov, NCT04624659 (v1), "A Study of FT-4202 in Adults and Adolescents With Sickle Cell Disease," Nov. 12, 2020.
ClinicalTrials.gov, NCT04624659 (v2), "A Study of FT-4202 in Adults and Adolescents With Sickle Cell Disease," Nov. 13, 2020.
Croasdell, G., European Hematology Association—20th Annual Congress (Jun. 11-14, 2015—Vienna, Austria) Meeting Report, Drugs of Today (2015), 51(7),I pp. 441-445.
Droxia [package insert]. Princeton, New Jersey, Bristol-Myers Squibb Company, (Dec. 2017), 28 pgs.
Droxia [package insert]. Princeton, New Jersey, Bristol-Myers Squibb Company (Dec. 2019), 25 pgs.
Endari [package insert]. Torrance, California: Emmaus Medical, Inc., (Jul. 2017), 8 pgs.
Endari [package insert]. Torrance, California, Emmaus Medical, Inc., (Nov. 2019), 10 pgs.
Estepp, et al., Phase 1 Single (SAD) and Multiple Ascending Dose (MAD) Study of the Safety, Pharmacokinetics (PK) and Pharmacodynamics (PD) of FT-4202, A PKR-Activator, In Healthy and Sickle Cell Disease Subjects, Abstract, e-Poster, European Hematology Association Open Access Library, Presentation EHA25, (May 14, 2020), 2 pgs.
Estepp, et al., Phase 1 Single (SAD) and Multiple Ascending Dose (MAD) Study of the Safety, Phyarmacokinetics (PK) and Pharmacodynamics (PD) of FT-4202, a PKR Activator, in Healthy and Sickle Cell Disease Subjects, Poster, EP1531, (Jun. 12, 2020), 1 pg.
Estepp, Jeremie H., et al., "Phase 1 Single (SAD) and Multiple Ascending Dose (MAD) Study of the Safety, Pharmacokinetics (PK) and Pharmacodynamics (PD) of FT-4202, a PKR Activator, in Healthy Volunteers and Patients with Sickle Cell Disease," Virtual meeting [poster EP1531] presented at the $25^{th}$ Congress of the European Hematology Association; Jul. 11-21, 2020.
European Hematology Association HemaSphere Abstract Book, $15^{th}$ Annual Sickle Cell & Thalassaemia & $1^{st}$ EHA European Sickle Cell Conference, Oct. 26-31, 2020.
Forma Therapeutics, Press Release, "Forma Therapeutics Presents Clinical Proof-of-Concept Data at the $62^{nd}$ Annual ASH Meeting Supporting the Potential of its Novel Investigational PKR Activator, FT-4202, to Treat Sickle Cell Disease (SCD)" (Dec. 7, 2020).
Grace, et al., Safety and Efficacy of Mitapivat in Pyruvate Kinase Deficiency, N. Engl. J. Med. 381, 10, (Sep. 5, 2019), p. 933-944.
Hydrea [package insert]. Princeton, New Jersey, Bristol-Myers Squibb Company (Jul. 2019), 29 pgs.
International Search Report and Written Opinion for PCT/US2019/052024, dated Dec. 23, 2019 (Dec. 23, 2019).
International Search Report for PCT/US2018/023405, 6 pages (dated Jun. 5, 2018).
International Search Report and Written Opinion from corresponding International Application No. PCT/US2020/051579, dated Dec. 10, 2020.
International Search Report and Written Opinion from corresponding International Application No. PCT/US2020/051645, dated Dec. 7, 2020.
Kalfa, T. A. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", JSCDH-D-20-0053, vol. VII, Pub. Date: Jun. 12, 2020; pp. 83-84.
Kalfa, T. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", $14^{th}$ Annual Sickle Cell Disease Research and Educational Symposium/$43^{rd}$ National Sickle Cell Disease Scientific Meeting (Sep. 23-25, 2020).
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin

(56) References Cited

OTHER PUBLICATIONS

SC Disease Irrespective of Prior Hydroxyurea Use," Blood (2020) 136 (Supplementl):23-24, Nov. 4, 2020.
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Presented at the 62$^{nd}$ American Society of Hematology (ASH) Annual Meeting, Dec. 5, 2020.
Le, Kha et al., Population pharmacokinetics and pharmacodynamics of AG-519, a pyruvate kinase activator for the treatment of pyruvate kinase deficiency, in human healthy volunteers, Agios Pharma—1263 Poster,—58th American Society of Hematology Annual Meeting and Exposition, Dec. 3-6, 2016—San Diego, CA.
Le, Kha et al., Population pharmacokinetics and pharmacodynamics of AG-519, a pyruvate kinase activator for the treatment of pyruvate kinase deficiency, Agios Pharma—3336 Poster,—57th American Society of Hematology Annual Meeting and Exposition, Dec. 5-8, 2015—Orlando, FL.
Lehrer-Graiwer, Josh et al., Long-Term Dosinig in Sickle Cell Disease Subjects with GBT440, a Novel HbS Polymerization Inhibitor, blood, 114, Hemoglobinopathies, Excluding Thalassemia—Clinical Poster II, Dec. 2, 2016.
OXBRYTA [package insert]. San Francisco, California, Global Blood Therapeutics, Inc. (Nov. 2019), 15 pgs.
OXBRYTA Slide Show—Jan. 2020.
Press Release—"Agios Announces New Data from AG-348 and AG-519 Demonstrating Potential for First Disease-modifying Treatment for Patients with PK Deficiency" Dec. 4 2016—Globe Newswire.
Press Release—"Agios Presents Updated Data from Drive PK Study Demonstrating AG-348 is Well-Tolerated and Results in Clinically Relevant, Rapid and Sustained Hemoglobin Increases in Patients with Pyruvate Kinase Deficiency" Dec. 10, 2017—Globe Newswire.
Rab, et al., AG-348 (Mitapivat), an allosteric activator of red blood cell pyruvate kinase, increases enzymatic activity, protein stability, and ATP levels over a broad range of PKLR genotypes, Haematologica, 105:xxx, (Jan. 23, 2020).
Reblozyl [package insert]. Cambridge, Massachusetts, Acceleron Pharma, Inc. (2020), 27 pgs.
Reblozyl [package insert]. Summit, New Jersey, Celgene Corporation (Nov. 2019), 16 pgs.
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Blood (2020) 136 (Supplement 1):21-22, Nov. 4, 2020.
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Presented at the 62nd American Society of Hematology (ASH) Annual Meeting, Dec. 5, 2020.
SIKLOS [package insert]. Lannoy, France, Delpharm Lille, (May 2019), 24 pgs.
SIKLOS [package insert]. Paris, France, Addmedica, (Dec. 2017), 25 pgs.
SIKLOS [package insert]. Paris, France, Addmedica, (May 2018), 23 pgs.
United States Securities and Exchange Commission, Form S-1, Registration Statement—Forma Therapeutics Holdings, Inc., May 29, 2020.
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease (PRAISE)," Blood (2020) 136 (Supplement 1):19-20, Nov. 4, 2020.
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease," Presented at the 62$^{nd}$ American Society of Hematology (ASH) Annual Meeting, Dec. 7, 2020.
Yang, H. et al., Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers, 8 Clin. Pharmacol. Drug Dev. 246-259 (2019).
Written Opinion of the International Searching Authority of PCT/US2018/023405, dated Jun. 5, 2018.

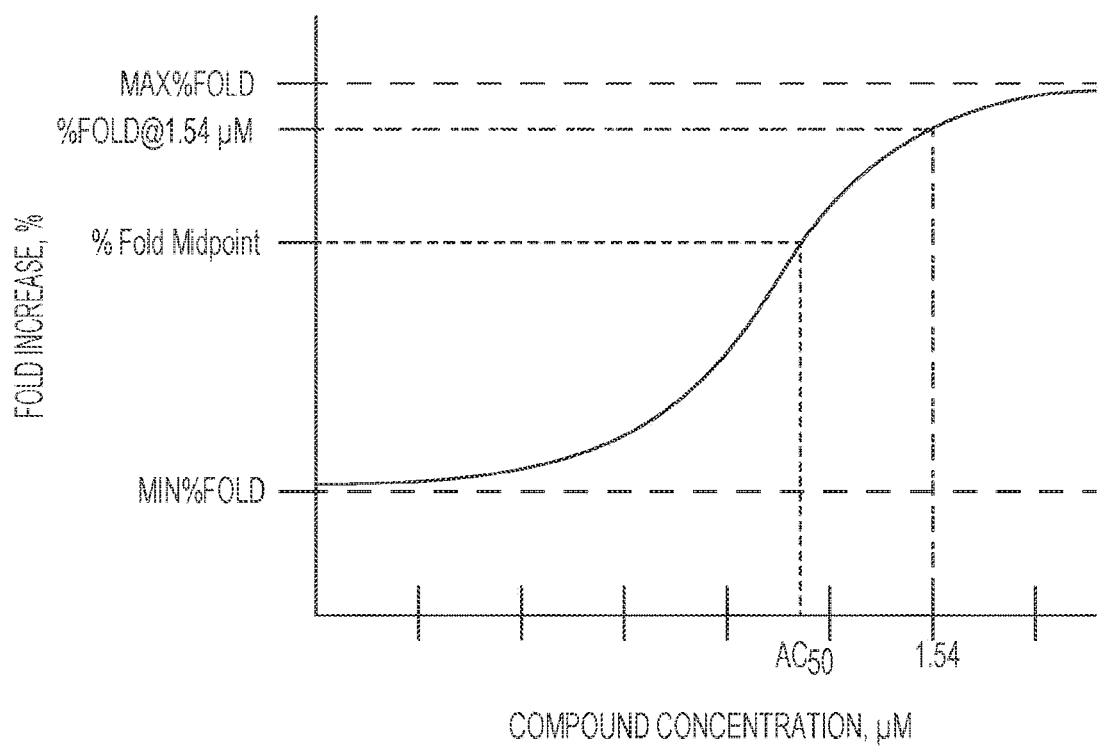

ACTIVATING PYRUVATE KINASE R AND MUTANTS THEREOF

CROSS-REFERENCE TO RELATED APPLICATION

This application claims the benefit of U.S. Provisional Application No. 62/733,546, filed on Sep. 19, 2018, which is incorporated herein by reference in its entirety.

TECHNICAL FIELD

This disclosure relates to novel chemical compositions for activating the pyruvate kinase enzyme, useful in the treatment of pyruvate kinase-related medical conditions (e.g., pyruvate kinase deficiency).

BACKGROUND

Pyruvate Kinase (PK) converts phosphoenolpyruvate (PEP) and adenosine diphosphate (ADP) to pyruvate and adenosine triphosphate (ATP), respectively, which is the final step in glycolysis. In humans, four PK isoforms are expressed by two structural genes. The PKLR gene encodes PKR and PKL, tissue specific isoforms expressed in erythroid cells and liver cells, respectively. The PKM gene codes for isoforms PKM1, expressed in brain and skeletal muscle, and PKM2 (M2-type pyruvate kinase), expressed in fetal and most adult tissues except erythroid cells.

Mutations in the PKLR gene can lead to pyruvate kinase deficiency (PKD), an autosomal recessive disorder, which is the most frequent enzymatic defect of the glycolytic pathway in erythrocytes. Over 200 different mutations have been identified on the structural PKLR gene. Generally, most PKD patients are heterozygous with two different mutant alleles, but homozygous mutations have also been described. Clinical symptoms of PKD vary considerably from mild to severe anemia. Mutations can reduce PK enzymatic activity or decrease PK protein stability. Pathological manifestations are usually observed when enzyme activity falls below 25% normal PK activity, and severe disease has been associated with a high degree of reticulocytosis. Although the global incidence of PKD is unknown, it has been estimated at 51 cases per million in North America. Heterogenous genetic mutations in PKR can lead to dysregulation of its catalytic activity. These mutations represent wide range genetic lesions that include deletional and transcriptional or translational abnormalities, including missense mutation in the coding region that can affect conserved residues within domains that are structurally important for optimal catalytic function of PKR.

Currently, there is no definitive treatment for severe PKD. Although splenectomy can be clinically useful in patients with severe disease, in some cases, allogeneic hematopoietic transplantation is required. In these patients, hematopoietic stem cell (HSC) gene therapy might be a good and more effective treatment. Gene therapy strategies for PKD have been addressed in animal models demonstrating that introduction of the correct version of the human PKLR gene into hematopoietic stem cells using retroviral vectors alleviates the disease. Although bone marrow transplant (BMT) or gene therapy strategies would be definitive treatments of the disease, they have yet to be realized clinically, and important adverse effects are associated with both approaches.

There remains a need for strategies to improve the treatment of diseases related to PKR, such as PKD, including the discovery and development of PKR activating small molecules. PKR exists in both a dimeric and tetrameric state, but functions most efficiently as a tetramer. Small molecules have been shown to be capable of shifting the equilibrium of PKR to the tetrameric (most active) form, providing a mechanistic rationale for their use as therapy for PKD-associated hemolytic anemia. Thus, there is a need for PKR activating compounds, useful for treating diseases and disorders associated with modulation of PKR and/or PKM2.

SUMMARY

The disclosure relates in part to compounds and compositions useful for activating PKR, including the discovery of a novel compound active with wild type (wt) PKR and/or mutant isozyme forms of PKR. For example, compounds and methods provided herein can be used for activating wild type PKR isozyme and/or a mutant PKR isozyme. Examples of mutant PKR isozyme include G332S, G364D, T384M, G37E, R479H, R479K, R486W, R532W, R510Q, I90N, and R490W. The invention is based in part on the discovery of a novel compound demonstrating activation of (wt) PKR and the G332S and R510Q mutant forms of PKR.

A PKR activator can be a compound identified as a PKR Activating Compound, defined herein as having one or more of the following characteristics when tested according to the Luminescence Assay Protocol of Example 3 below: (1) an $AC_{50}$ value of less than 40 µM; (2) a maximum % Fold (MAX % Fold) value of greater than 75%; and/or (3) a % Fold value at 1.54 µM compound concentration (% Fold@1.54 µM) of at least 75%. In some embodiments, the PKR Activating Compound has: (1) an $AC_{50}$ value of less than 0.1 µM, 0.1-1.0 µM, or 1.01-40 µM; (2) a MAX % Fold of 75%-250%, 251-500%, or 75%-500%; and/or (3) a % Fold@1.54 µM of 75%-250%, 251-500%, or 75%-500%. In some embodiments, a PKR Activating Compound has (1) an $AC_{50}$ value of less than 1.0 µM; (2) a MAX % Fold of 75%-500%; and/or (3) a % Fold@1.54 µM of 75%-500%. In some embodiments, the Luminescence Assay Protocol of Example 3 is performed with wild type (wt) PKR, G332S mutant form of PKR or R510Q mutant form of PKR. In some embodiments, a PKR Activating Compound can be the compound (2R)-2-hydroxy-2-phenyl-1-[5-(pyridine-2-sulfonyl)-1H,2H,3H,4H, 5H,6H-pyrrolo[3,4-c]pyrrol-2-yl]ethan-1-one (Compound 1):

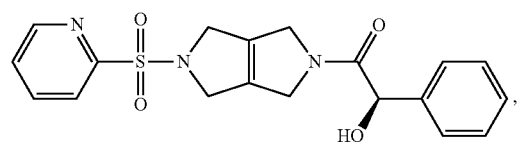

or a pharmaceutically acceptable salt thereof, having (1) an $AC_{50}$ value of less than 1.0 µM; (2) a MAX % Fold of 75%-500%; and/or (3) a % Fold@1.54 µM of 75%-500%.

A method for treating pyruvate kinase deficiency (PKD) in a subject in need thereof, comprising administering to the subject a therapeutically effective amount of: (a) Compound 1 or a pharmaceutically acceptable salt thereof; (b) a composition comprising Compound 1 or a salt thereof and a carrier; or (c) a pharmaceutical composition comprising Compound 1 or a pharmaceutically acceptable salt thereof, and a pharmaceutically acceptable carrier, to thereby treat PKD in the subject. The method can include or result in activating one or more isozymes of pyruvate kinase. One or more isozymes of pyruvate kinase can be selected from PKR, PKM2, and PKL; the method can also include or result in activating a mutant PKR isozyme.

BRIEF DESCRIPTION OF THE DRAWING

FIG. 1 shows an exemplary dose-response curve for compounds disclosed herein. Dose-response curves may be generated using the standard four parameter fit algorithm of ActivityBase XE Runner to determine MAX % Fold, MIN % Fold, slope and $AC_{50}$. MAX % Fold is the highest % fold increase observed at any concentration of compound, and MIN % Fold is the lowest % fold increase observed at any concentration of compound. The $AC_{50}$ value for a compound is the concentration (μM) corresponding to the midway between the maximum and minimum values of the four parameter logistic curve fit (i.e., at which the % fold increase along the four parameter logistic curve fit is halfway between MAX % Fold and MIN % Fold (% Fold Midpoint). Another useful parameter for evaluating compounds of this disclosure is % Fold@1.54 which is the % fold increase at a compound concentration of 1.5 μM (e.g., 1.54 X-axis and y-axis not necessarily to scale.

DETAILED DESCRIPTION

In some embodiments, the present disclosure provides a PKR Activating Compound which is Compound 1:

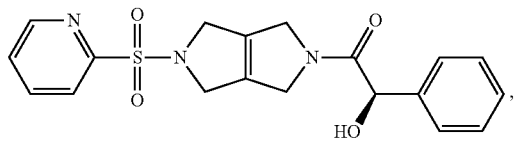

1 or a pharmaceutically acceptable salt thereof. In some embodiments, the PKR Activating Compound is (2R)-2-hydroxy-2-phenyl-1-[5-(pyridine-2-sulfonyl)-1H,2H,3H, 4H,5H,6H-pyrrolo[3,4-c]pyrrol-2-yl]ethan-1-one. Compound 1 is useful for the activation of PKR and mutant isozyme forms thereof.

The present disclosure also provides compositions (e.g. pharmaceutical compositions) comprising Compound 1. The pharmaceutical compositions provided herewith may be orally administered in any orally acceptable dosage form including, but not limited to, capsules, and tablets (e.g., in unit dosage forms). In some embodiments, Compound 1 is formulated for oral administering to the subject at a dose of about 10 mg to about 1000 mg, e.g., as a capsule or tablet containing about 50 mg-about 100 mg of Compound 1 and pharmaceutically acceptable carriers and/or excipients. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician. Pharmaceutical compositions of Compound 1 may comprise one or more additional excipients and/or carriers, with Compound 1 present at dosage levels of between about 1 to 100%, and more preferably between about 5 to 95% by weight of the pharmaceutical composition.

Compounds and compositions described herein are activators of wild type PKR and certain PKR mutants having lower activities compared to the wild type. Such mutations in PKR can affect enzyme activity (catalytic efficiency), regulatory properties and/or thermostability of the enzyme. One example of a PKR mutation is G332S. Another example of a PKR mutation is R510Q. Methods of treatment (e.g., by activating wild type PKR) can comprise administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof and a pharmaceutically acceptable carrier. The pharmaceutical compositions may be orally administered in any orally acceptable dosage form. In some embodiments, to increase the lifetime of red blood cells, a compound, composition or pharmaceutical composition described herein is added directly to whole blood or packed cells extracorporeally or provided to the subject (e.g., the patient) directly. The compositions described herein can modulate (e.g., activate) PKR. Accordingly, a patient and/or subject can be selected for treatment using a compound described herein by first evaluating the patient and/or subject to determine whether the subject is in need of modulation (e.g., activation) of PKR, and if the subject is determined to be in need of modulation of PKR, then administering to the subject a composition described herein.

Compound 1 can activate wild type PKR and/or mutant PKRs. Some examples of the mutant PKRs include G332S, G364D, T384M, G37E, R479H, R479K, R486W, R532W, R510Q, I90N, and R490W. Accordingly, a patient and/or subject can be selected for treatment using Compound 1 by first evaluating the patient and/or subject to determine whether the subject carries a mutation in PKR (for example, one of the mutations as described herein), and if the subject is determined to be carrying a mutation in PKR thus is in need of activation of the activity of the mutant PKR, then administering to the subject a therapeutically effective amount of Compound 1. A subject can be evaluated as carrying a mutation in PKR using methods known in the art. The subject can also be monitored, for example, subsequent to administration of Compound 1.

A patient can be monitored for evaluation of certain PK/PD parameters of Compound 1 such as levels of Compound 1, levels of 2,3-DPG, or levels of ATP.

In some embodiments, the disclosure relates to a method of treating a patient diagnosed with a pyruvate kinase-related medical condition, the method comprising administering to the patient in need thereof a therapeutically effective amount of a PKR Activating Compound having a maximum % Fold (MAX % Fold) value of greater than 75%. In some embodiments, the disclosure relates to a method of treating a patient diagnosed with a pyruvate kinase-related medical condition, the method comprising administering to the patient in need thereof a therapeutically effective amount of a PKR Activating Compound having a % Fold value at 1.54 μM compound concentration (% Fold@1.54 μM) of at least 75%.

In one aspect, the present invention provides a method of treating a subject, the method comprising: administering to the subject (2R)-2-Hydroxy-2-phenyl-1-(5-(pyridin-2-ylsulfonyl)-3,4,5,6-tetrahydropyrrolo[3,4-c]pyrrol-2(1H)-yl)ethan-1-one (Compound 1); and acquiring a value for the level of Compound 1, the level of 2,3-diphosphoglycerate (2,3-DPG), the level of adenosine triphosphate (ATP), or the activity of PKR in the subject, to thereby evaluate the subject. The value for the level of Compound 1 can be acquired by analyzing the plasma concentration of Compound 1. In some embodiments, the level of 2,3-DPG is acquired by analyzing the blood concentration of 2,3-DPG. The level of ATP can be acquired by analyzing the blood concentration of ATP. The activity of PKR can be acquired by analyzing the blood concentration of a $^{13}$C-label in the blood. For example, $^{13}$C-labeled glucose is administered to a subject, and incorporated into certain glycolytic intermediates in the blood.

A method of treatment can comprise administering an amount of Compound 1 sufficient to provide a blood concentration of 2,3-DPG that is reduced by at least 15% relative to the reference standard (e.g., from about 15% to about 60%). In some embodiments, the blood concentration of 2,3-DPG is reduced by at least about 15%, by at least about 20%, by at least about 25%, by at least about 30%, by at least about 35%, by at least about 40%, by at least about 45%, by at least about 50%, by at least about 55%, by at least about 60%. In some embodiments, the analysis is performed by sample analysis of bodily fluid, such as blood, by e.g., mass spectroscopy, e.g. LC-MS.

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description and drawings are by way of example to illustrate the discoveries provided herein.

EXAMPLES

Example 1: Synthesis of (2R)-2-Hydroxy-2-phenyl-1-(5-(pyridin-2-ylsulfonyl)-3,4,5,6-tetrahydropyrrolo[3,4-c]pyrrol-2(1H)-yl)ethan-1-one Intermediate A: tert-Butyl 5-(pyridin-2-ylsulfonyl)-3,4,5,6-tetrahydropyrrolo[3,4-c]pyrrole-2(1H)-carboxylate

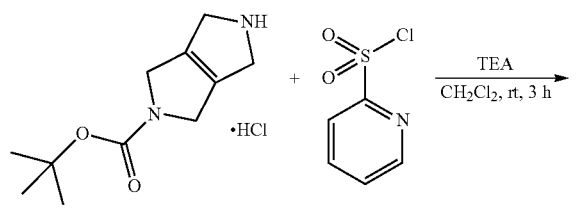

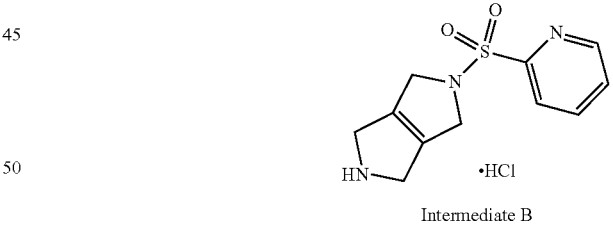

Intermediate A

To a suspension of tert-butyl 3,4,5,6-tetrahydropyrrolo[3,4-c]pyrrole-2(1H)-carboxylate, HCl (1.10 g, 4.46 mmol) in dichloromethane (25 mL) at room temperature was added TEA (1.49 mL, 10.7 mmol) followed by pyridine-2-sulfonyl chloride (0.950 g, 5.35 mmol). The reaction mixture was stirred at room temperature for 3 hours. The solvent was removed under reduced pressure and the residue was taken up in EtOAc (50 mL). The organic mixture was sequentially washed with water (50 mL) and saturated aqueous sodium chloride solution (50 mL). The organic layer was collected, dried over sodium sulfate, filtered and concentrated under reduced pressure. The crude material was purified by silica gel column chromatography (0% EtOAc/hexane for 5 min then 0-75% EtOAc/hexane for 30 min) to afford tert-butyl 5-(pyridin-2-ylsulfonyl)-3,4,5,6-tetrahydropyrrolo[3,4-c]pyrrole-2(1H)-carboxylate (0.57 g, 1.622 mmol, 36.4% yield). LCMS (m/z, M+H+) 351.9, 1H-NMR (300 MHz, CDCl3): δ ppm 8.69 (m, 1H), 8.00-7.88 (m, 2H), 7.49 (m, 1H), 4.33 (m, 4H), 4.05 (m, 4H), 1.45 (s, 9H).

Intermediate B: 2-(Pyridin-2-ylsulfonyl)-1,2,3,4,5,6-hexahydropyrrolo[3,4-c]pyrrole, HCl

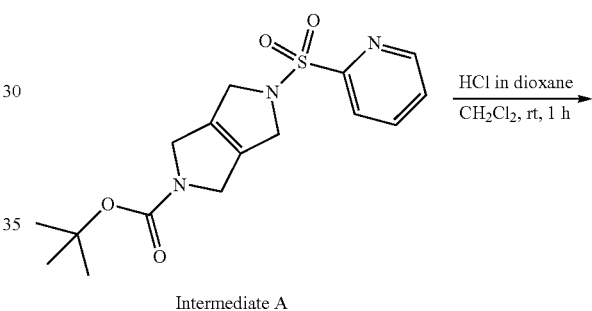

Intermediate B

To a solution of tert-butyl 5-(pyridin-2-ylsulfonyl)-3,4,5,6-tetrahydropyrrolo[3,4-c]pyrrole-2(1H)-carboxylate (0.570 g, 1.62 mmol) in dichloromethane (4.96 ml) was added 4 M HCl/dioxane (17.6 ml). The reaction mixture was stirred at room temperature for 1 hour. The reaction mixture was concentrated under reduced pressure then triturated with ether. The white solid was filtered off to give 2-(pyridin-2-ylsulfonyl)-1,2,3,4,5,6-hexahydropyrrolo[3,4-c]pyrrole, HCl (0.547 g, 1.90 mmol, quantitative yield) that was used in the next step without further purification. LCMS (m/z, M+H+) 252.0, 1H-NMR (300 MHz, DMSO-d6): δ ppm 9.99 (br m, 2H), 8.75 (m, 1H), 8.13 (m, 1H), 7.97 (m, 1H), 7.71 (m 1H), 4.24 (m, 4H), 3.89 (m, 4H).

(R)-2-Hydroxy-2-phenyl-1-(5-(pyridin-2-ylsulfo-nyl)-3,4,5,6-tetrahydropyrrolo[3,4-c]pyrrol-2(1H)-yl)ethan-1-one

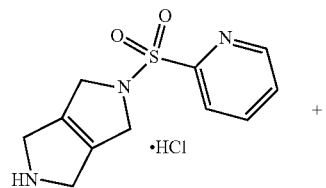

Intermediate B

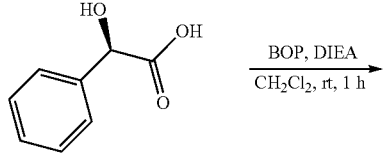

Compound 1

To a suspension of 2-(pyridin-2-ylsulfonyl)-1,2,3,4,5,6-hexahydropyrrolo[3,4-c]pyrrole, HCl (0.547 g, 1.90 mmol) in dichloromethane (12.6 mL) was added (R)-2-hydroxy-2-phenylacetic acid (0.241 g, 1.58 mmol), BOP (0.771 g, 1.74 mmol) and DIEA (0.830 ml, 4.75 mmol). The reaction mixture was stirred at room temperature for 2 hours. Ethyl acetate (50 mL) was added and the organic phase was washed with saturated aqueous sodium hydrogen carbonate solution (50 mL) and saturated aqueous sodium chloride solution (50 mL). The organic phase was dried over magnesium sulfate, filtered, and concentrated under reduced pressure. The crude material was purified by silica gel column chromatography on (gradient of 0-10% MeOH/dichloromethane) to afford (R)-2-hydroxy-2-phenyl-1-(5-(pyridin-2-ylsulfonyl)-5,6-dihydropyrrolo[3,4-c]pyrrol-2(1H,3H,4H)-yl)ethanone (0.353 g, 0.916 mmol, 57.8% yield). LCMS (m/z, M+H+) 385.9, 1H-NMR (300 MHz, DMSO-d6): δ ppm 8.69 (m, 1H), 8.07 (m, 1H), 7.91 (m, 1H), 7.68-7.64 (m, 1H), 7.33-7.26 (m, 5H), 5.64 (d, J=6.0 Hz, 1H), 5.14 (d, J=6.3 Hz, 1H), 4.30-3.88 (m, 8H).

Example 2. 1-(5-[[4-(Difluoromethoxy)benzene]sulfonyl]-1H,2H,3H,4H,5H,6H-pyrrolo[3,4-c]pyrrol-2-yl)-2-hydroxy-2-(pyridin-3-yl)ethan-1-one

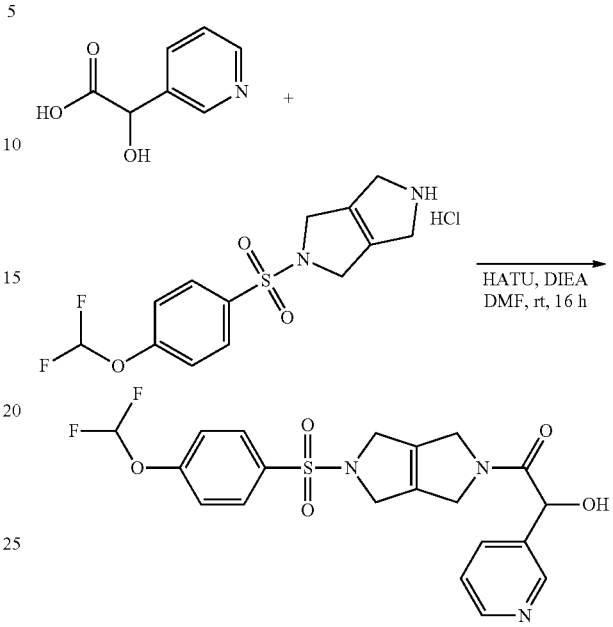

Example 2

Into a 8-mL vial (1 atm), was placed a mixture of 2-hydroxy-2-(pyridin-3-yl)acetic acid (39.8 mg, 0.26 mmol, 1.30 equiv), N,N-dimethylformamide (1.5 mL), 2-((4-(difluoromethoxy)phenyl)sulfonyl)-1,2,3,4,5,6-hexahydropyrrolo[3,4-c]pyrrolehydrochloride (70.6 mg, 0.20 mmol, 1.00 equiv), DIEA (65 mg, 0.50 mmol, 2.50 equiv) and HATU (91 mg, 0.24 mmol, 1.20 equiv). The resulting solution was stirred for 16 h at room temperature. The reaction solution was diluted with 50 mL of ethyl acetate, washed with 4×10 mL of brine, dried over anhydrous sodium sulfate and concentrated under vacuum. The crude product was purified by prep-TLC. This resulted in 1-(5-[[4-(Difluoromethoxy)benzene]sulfonyl]-1H,2H,3H,4H,5H, 6H-pyrrolo[3,4-c]pyrrol-2-yl)-2-hydroxy-2-(pyridin-3-yl)ethan-1-one as an off-white solid. 1H NMR (300 MHz, CDCl3): δ ppm 8.66 (d, J=4.8 Hz, 1H), 8.65-7.87 (m, 2H), 7.51-7.48 (m, 1H), 7.48-7.31 (m, 5H), 5.01 (s, 1H), 4.32-4.15 (m, 7H), 3.63 (d, J=12.3 Hz, 1H). LCMS m/z: 452 [M+H]+.

Compound 1 in Table 1 below was prepared according to the procedure outlined above for Example 2, using the appropriate synthetic precursors.

TABLE 1

| Example | Structure Name | LCMS (m/z) | 1H-NMR |
|---|---|---|---|
| Compound 1 | (2R)-2-hydroxy-2-phenyl-1-[5-(pyridine-2-sulfonyl)-1H,2H,3H,4H,5H,6H-pyrrolo[3,4-c]pyrrol-2-yl]ethan-1-one | 386 | (300 MHz, CDCl3): δ ppm 8.66 (d, J = 4.8 Hz, 1H), 8.65-7.87 (m, 2H), 7.51-7.48 (m, 1H), 7.48-7.31 (m, 5H), 5.01 (s, 1H), 4.32-4.15 (m, 7H), 3.63 (d, J = 12.3 Hz, 1H) |

Example 3. Luminescence Biochemical Assay

In some embodiments, a PKR Activating Compound refers to a compound having one or more characteristics when tested according to the following Luminescence Assay Protocol of Example 3 performed with wild type (wt) PKR and/or any one or more of G332S mutant form of PKR or R510Q mutant form of PKR: (1) an $AC_{50}$ value of less than 40 µM (e.g., compounds with $AC_{50}$ values of "+", "++", or "+++" in Table 2); (2) a maximum % Fold (MAX % Fold) value of greater than 75%; and/or (3) a % Fold value at 1.54 µM compound concentration (% Fold@1.54 µM) of at least 75%. In some embodiments, a PKR Activating Compound can have: (1) an $AC_{50}$ value of less than 0.1 µM (e.g., compounds with $AC_{50}$ values of "+++" in Table 2), 0.1-1.0 µM (e.g., compounds with $AC_{50}$ values of "++" in Table 2), or 1.01-40 µM (e.g., compounds with $AC_{50}$ values of "+" in Table 2); (2) a MAX % Fold of 75%-250%, 250-500%, or 75%-500%; and/or (3) a % Fold@1.54 µM of 75%-250%, 250-500%, or 75%-500%. In some embodiments, a PKR Activating Compound has (1) an $AC_{50}$ value of less than 1.0 µM; (2) a MAX % Fold of 75%-500%; and/or (3) a % Fold@1.54 µM of 75%-500%.

The phosphorylation of Adenosine-5'-diphosphate (ADP) by various mutants of PKR was determined by the Kinase Glo Plus Assay (Promega) in the presence or absence of FBP [D-Fructose-1,6-diphosphate; BOC Sciences, CAS: 81028-91-3] as follows. Unless otherwise indicated, all reagents were purchased from Sigma-Aldrich. All reagents were prepared in buffer containing 50 mM Tris-HCl, 100 mM KCl, 5 mM $MgCl_2$, and 0.01% Triton X100, 0.03% BSA, and 1 mM DTT. Enzyme and PEP [Phospho(enol) pyruvic acid] were added at 2× to all wells of an assay-ready plate containing serial dilutions of test compounds or DMSO vehicle. Final enzyme concentrations for PKR(wt), PKR (R510Q), and PKR(G332S) were 0.8 nM, 0.8 nM, and 10 nM respectively. Final PEP concentration was 100 µM. The Enzyme/PEP mixture was incubated with compounds for 30 minutes at RT before the assay was initiated with the addition of 2×ADP [Adenosine-5'-diphosphate] and Kinase-GloPlus. Final concentration of ADP was 100 µM. Final concentration of KinaseGloPlus was 12.5%. For assays containing FBP, that reagent is added at 30 µM upon reaction initiation. Reactions were allowed to progress for 45 minutes at RT until luminescence was recorded by the BMG PHERAstar FS Multilabel Reader. All compounds were tested in triplicate at concentrations ranging from 42.5 µM to 2.2 nM in 0.83% DMSO.

Luminescence values were converted to % Fold increase by normalizing to the average of the DMSO control and multiplying by 100. Max, min, slope and $AC_{50}$ were determined by the standard four parameter fit algorithm of ActivityBase XE Runner. Compounds were evaluated with three parameters—$AC_{50}$, MAX % Fold, and % Fold@1.54 µM (FIG. 1). The $AC_{50}$ value for a compound is the concentration (µM) corresponding to the midway between the maximum and minimum values of the four parameter logistic curve fit (i.e., at which the % fold increase along the four parameter logistic curve fit is halfway between MAX % Fold and MIN % Fold (% Fold Midpoint)), MAX % Fold is the highest fold increase observed at any concentration of compound, and % Fold@1.54 µM is the fold increase at a compound concentration of 1.54 µM. The parameter % Fold@1.54 µM was selected to capture elements of both the $AC_{50}$ and MAX % Fold and to provide a ranking based on both potency and effect. The compound concentration of 1.54 µM was chosen as one that can optimally differentiate the set of compounds based on the range of activities observed.

As set forth in Table 2 below, $AC_{50}$ values (columns A, D, G) are defined as follows: ≤0.1 µM (+++); >0.1 µM and ≤1.0 µM (++); >1.0 µM and ≤40 µM (+); >40 µM (0). Max % FOLD values (columns B, E, H) are defined as follows: ≤75% (+); >75% and ≤250% (++); >250% and ≤500% (+++). % Fold@1.54 µM values (columns C, F, J) are defined as follows: ≤75% (+); >75% and ≤250% (++); >250% and ≤500% (+++).

TABLE 2

| Compound | PKRG332S Conditions[1] | | | PKRR510Q Conditions[1] | | | WT Conditions[1] | | |
|---|---|---|---|---|---|---|---|---|---|
| | A | B | C | D | E | F | G | H | J |
| 1 | ++ | ++ | ++ | ++ | +++ | ++ | +++ | ++ | ++ |

[1]A—AC50 LUM KGP FBP $AC_{50}$ µM gmean;
B—AC50 LUM KGP FBP MAX % FOLD mean;
C—AC50 LUM KGP FBP % Fold@1.54 µM mean
D—AC50 LUM KGP woFBP $AC_{50}$ µM gmean;
E—AC50 LUM KGP woFBP MAX % FOLD mean;
F—AC50 LUM KGP woFBP % Fold@1.54 µM mean
G—AC50 LUM KGP woFBP $AC_{50}$ µM gmean;
H—AC50 LUM KGP woFBP MAX % FOLD mean;
J—AC50 LUM KGP woFBP % Fold@1.54 µM mean

TABLE 3

Biological Data of Additional Compounds

| Compound | Structure | PKR G332S Conditions[1] A | PKR R510Q D | wt G |
|---|---|---|---|---|
| 23 | 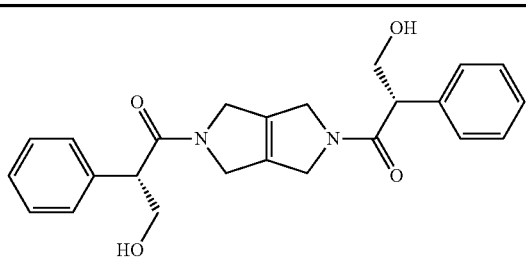 | 0 | 0 | |

TABLE 3-continued
Biological Data of Additional Compounds
| | | PKR G332S | PKR R510Q | wt |
| | | Conditions[1] | | |
| Compound | Structure | A | D | G |
| 24 | 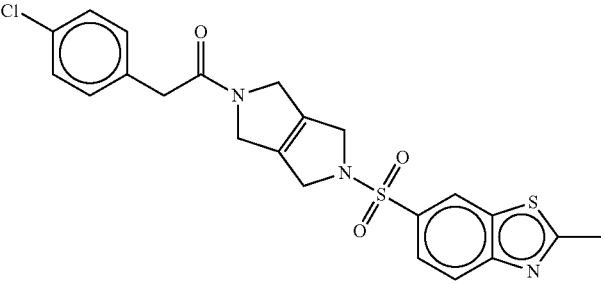 | | | + |
| 25 | 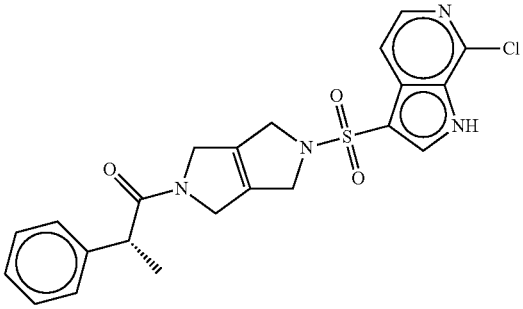 | + | + | |
| 26 | 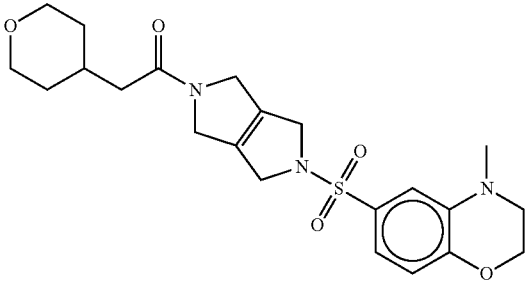 | | | + |
| 27 | 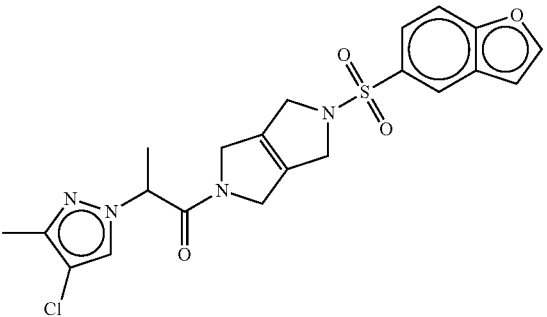 | | | + |

TABLE 3-continued

Biological Data of Additional Compounds

| | | PKR G332S | PKR R510Q | wt |
| | | Conditions[1] | | |
| Compound | Structure | A | D | G |
| 28 | 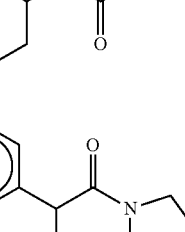 | | | + |
| 29 |  | | | + |
| 30 |  | + | + | + |

[1]A—AC50 LUM KGP FBP AC$_{50}$ μM gmean;
D—AC50 LUM KGP woFBP AC$_{50}$ μM gmean.
G—AC50 LUM KGP woFBP AC$_{50}$ μM gmean;

We claim:

1. A composition comprising Compound 1, or a pharmaceutically acceptable salt thereof:

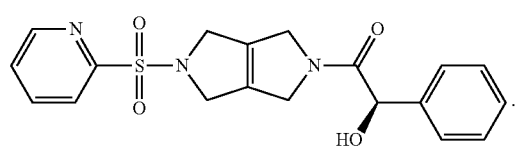

2. The composition of claim 1, formulated as an oral unit dosage form.

3. The composition of claim 1, comprising Compound 1 obtainable by a process comprising the step of converting Intermediate B into Compound 1 in a reaction:

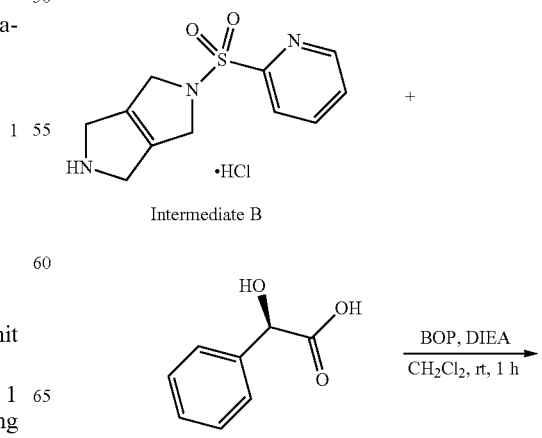

-continued

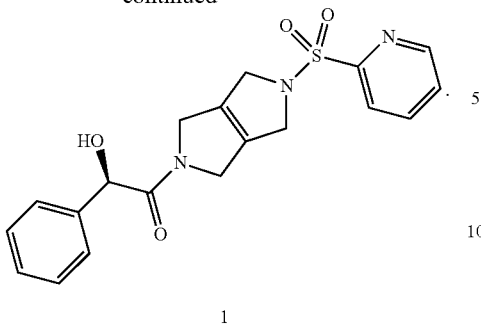

1

4. The composition of claim 3, wherein the process further comprises first obtaining Intermediate B from Intermediate A in a reaction:

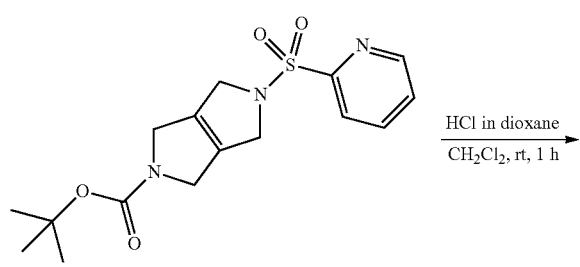

5. A method for treating pyruvate kinase deficiency (PKD) in a subject in need thereof, comprising administering to the subject a therapeutically effective amount of:
   a. Compound 1 or a pharmaceutically acceptable salt thereof;

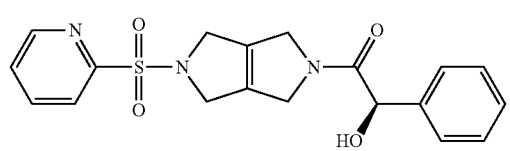

b. a composition comprising Compound 1 or a salt thereof and a carrier; or c. a pharmaceutical composition comprising Compound 1 or a pharmaceutically acceptable salt thereof, and a pharmaceutically acceptable carrier, to thereby treat PKD in the subject.

6. The method of claim 5, wherein the method comprises activating one or more isozymes of pyruvate kinase.

7. The method of claim 6, wherein the one or more isozymes of pyruvate kinase is selected from PKR, PKM2, and PKL.

8. The method of claim 5, wherein the method comprises activating a mutant PKR isozyme.

9. The method of claim 5, wherein the method comprises administering to the subject a therapeutically effective amount of Compound 1 or a pharmaceutically acceptable salt thereof.

10. The method of claim 9, wherein Compound 1 or a pharmaceutically acceptable salt thereof is administered orally.

11. The method of claim 5, wherein the method comprises administering to the subject a therapeutically effective amount of a composition comprising Compound 1 or a salt thereof and a carrier.

12. The method of claim 11, wherein the composition is administered orally.

13. The method of claim 5, wherein the method comprises administering to the subject a therapeutically effective amount of a pharmaceutical composition comprising Compound 1 or a pharmaceutically acceptable salt thereof, and a pharmaceutically acceptable carrier, to thereby treat PKD in the subject.

14. The method of claim 13, wherein the pharmaceutical composition is administered orally.

15. Compound 1:

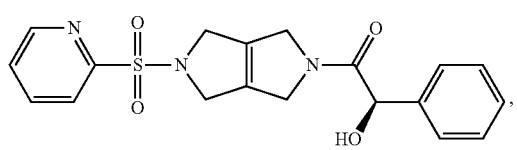

or a pharmaceutically acceptable salt thereof.

* * * * *